US012653564B2

(12) United States Patent (10) Patent No.: US 12,653,564 B2

Allen, IV et al. (45) Date of Patent: Jun. 16, 2026

(54) SURGICAL INSTRUMENT FOR TREATING TISSUE

(71) Applicant: Covidien LP, Mansfield, MA (US)

(72) Inventors: James D. Allen, IV, Broomfield, CO
(US); John R. Twomey, Longmont, CO
(US); Michael B. Lyons, Boulder, CO
(US); Jessica E.C. Olson, Frederick,
CO (US); Sean T. O'Neill, Los Gatos,
CA (US); Grant T. Sims, Lakewood,
CO (US)

(73) Assignee: Covidien LP, Mansfield, MA (US)

( * ) Notice: Subject to any disclaimer, the term of this
patent is extended or adjusted under 35
U.S.C. 154(b) by 182 days.

(21) Appl. No.: 18/757,674

(22) Filed: Jun. 28, 2024

(65) Prior Publication Data

US 2024/0350158 A1 Oct. 24, 2024

Related U.S. Application Data

(60) Continuation of application No. 16/817,935, filed on
Mar. 13, 2020, now Pat. No. 12,059,166, which is a
(Continued)

(51) Int. Cl.
*A61B 17/295* (2006.01)
*A61B 17/28* (2006.01)
(Continued)

(52) U.S. Cl.
CPC ........ *A61B 17/282* (2013.01); *A61B 17/3205*
(2013.01); *A61B 18/1445* (2013.01);
(Continued)

(58) Field of Classification Search
CPC ... A61B 17/282; A61B 17/3205; A61B 17/29;
A61B 17/295; A61B 18/1445;
(Continued)

(56) References Cited

U.S. PATENT DOCUMENTS 2,801,633 A 8/1957 Ehrlich
3,522,809 A 8/1970 Cornell
(Continued)

FOREIGN PATENT DOCUMENTS

CN 100493469 C 6/2009
CN 201299462 Y 9/2009
(Continued)

OTHER PUBLICATIONS

Japanese Office Action and English language translation from Appl.
No. 2013-095176 dated Apr. 6, 2017.
(Continued)

*Primary Examiner* — Katherine M Rodjom

(57) ABSTRACT

A surgical instrument includes an elongated shaft having a
distal portion and a proximal portion coupled to a housing.
An inner shaft member extends at least partially through the
elongated shaft and is selectively movable in a longitudinal
direction. An end effector is supported by the distal portion
of the elongated shaft. The end effector includes upper and
lower jaw members pivotally coupled to the distal portion of
the elongated shaft about a pivot axis and including a pair of
laterally spaced flanges. The pairs of flanges of the jaw
members are arranged in an offset configuration such that
one flange of the upper jaw member is positioned on a
laterally exterior side of a corresponding flange of the lower
jaw member, and the other flange of the upper jaw member
is positioned on a laterally interior side of the other flange of
the lower jaw member.

20 Claims, 14 Drawing Sheets

Related U.S. Application Data continuation of application No. 15/844,821, filed on Dec. 18, 2017, now Pat. No. 10,588,651, which is a continuation of application No. 15/013,096, filed on Feb. 2, 2016, now Pat. No. 9,861,378, which is a division of application No. 13/461,335, filed on May 1, 2012, now Pat. No. 9,820,765.

(51) Int. Cl.

| | |
|---|---|
| *A61B 17/3205* | (2006.01) |
| *A61B 18/14* | (2006.01) |
| *A61B 17/00* | (2006.01) |
| *A61B 17/29* | (2006.01) |
| *A61B 18/00* | (2006.01) |
| *A61B 90/00* | (2016.01) |

(52) U.S. Cl.
CPC ..... *A61B 2017/00526* (2013.01); *A61B 17/29* (2013.01); *A61B 2017/292* (2013.01); *A61B 2017/2936* (2013.01); *A61B 17/295* (2013.01); *A61B 2018/0063* (2013.01); *A61B 2018/1455* (2013.01); *A61B 2090/031* (2016.02); *Y10T 29/49826* (2015.01)

(58) Field of Classification Search
CPC .... A61B 2017/00526; A61B 2017/292; A61B 2017/2936; A61B 2018/1455
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| 5,383,471 A | 1/1995 | Funnell |
| D358,887 S | 5/1995 | Feinberg |
| 5,478,347 A | 12/1995 | Aranyi |
| 5,486,189 A | 1/1996 | Mudry et al. |
| 5,522,830 A | 6/1996 | Aranyi |
| 5,591,188 A | 1/1997 | Waisman |
| D384,413 S | 9/1997 | Zlock et al. |
| 5,707,392 A | 1/1998 | Kortenbach |
| 5,772,641 A | 6/1998 | Wilson |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| 6,117,158 A | 9/2000 | Measamer et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| 7,083,618 B2 | 8/2006 | Couture et al. |
| 7,090,673 B2 | 8/2006 | Dycus et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| D531,311 S | 10/2006 | Guerra et al. |
| 7,131,971 B2 | 11/2006 | Dycus et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinge |
| D541,938 S | 5/2007 | Kerr et al. |
| D545,432 S | 6/2007 | Watanabe |
| D547,154 S | 7/2007 | Lee |
| 7,255,697 B2 | 8/2007 | Dycus et al. |
| D564,662 S | 3/2008 | Moses et al. |
| D567,943 S | 4/2008 | Moses et al. |
| 7,384,420 B2 | 6/2008 | Dycus et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 7,766,910 B2 | 8/2010 | Hixson et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| 8,070,748 B2 | 12/2011 | Hixson et al. |
| D661,394 S | 6/2012 | Romero et al. |
| 8,246,618 B2 | 8/2012 | Bucciaglia et al. |
| 8,333,765 B2 | 12/2012 | Johnson et al. |
| 8,454,602 B2 | 6/2013 | Kerr et al. |
| 8,523,898 B2 | 9/2013 | Bucciaglia et al. |
| 8,529,566 B2 | 9/2013 | Kappus et al. |
| 8,568,408 B2 | 10/2013 | Townsend et al. |
| 8,591,510 B2 | 11/2013 | Allen, IV et al. |
| 8,628,557 B2 | 1/2014 | Collings et al. |
| 8,679,098 B2 | 3/2014 | Hart |
| 8,679,140 B2 | 3/2014 | Butcher |
| 8,685,009 B2 | 4/2014 | Chernov et al. |
| 8,685,056 B2 | 4/2014 | Evans et al. |
| 8,696,667 B2 | 4/2014 | Guerra et al. |
| 8,702,737 B2 | 4/2014 | Chojin et al. |
| 8,702,749 B2 | 4/2014 | Twomey |
| 8,745,840 B2 | 6/2014 | Hempstead et al. |
| 8,747,413 B2 | 6/2014 | Dycus |
| 8,747,434 B2 | 6/2014 | Larson et al. |
| 8,752,264 B2 | 6/2014 | Ackley et al. |
| 8,756,785 B2 | 6/2014 | Allen, IV et al. |
| 8,845,636 B2 | 9/2014 | Allen, IV et al. |
| 8,852,185 B2 | 10/2014 | Twomey |
| 8,864,753 B2 | 10/2014 | Nau, Jr. et al. |
| 8,864,795 B2 | 10/2014 | Kerr et al. |
| 8,887,373 B2 | 11/2014 | Brandt et al. |
| 8,888,771 B2 | 11/2014 | Twomey |
| 8,900,232 B2 | 12/2014 | Ourada |
| 8,920,461 B2 | 12/2014 | Unger et al. |
| 8,939,972 B2 | 1/2015 | Twomey |
| 8,961,513 B2 | 2/2015 | Allen, IV et al. |
| 8,961,514 B2 | 2/2015 | Garrison |
| 8,961,515 B2 | 2/2015 | Twomey et al. |
| 8,968,283 B2 | 3/2015 | Kharin |
| 8,968,298 B2 | 3/2015 | Twomey |
| 8,968,305 B2 | 3/2015 | Dumbauld et al. |
| 8,968,306 B2 | 3/2015 | Unger |
| 8,968,307 B2 | 3/2015 | Evans et al. |
| 8,968,308 B2 | 3/2015 | Horner et al. |
| 8,968,309 B2 | 3/2015 | Roy et al. |
| 8,968,310 B2 | 3/2015 | Twomey et al. |
| 8,968,311 B2 | 3/2015 | Allen, IV et al. |
| 8,968,317 B2 | 3/2015 | Evans et al. |

(56) References Cited

U.S. PATENT DOCUMENTS

| | | | |
|---|---|---|---|
| 8,968,360 | B2 | 3/2015 | Garrison et al. |
| 9,011,435 | B2 | 4/2015 | Brandl et al. |
| 9,023,035 | B2 | 5/2015 | Allen, IV et al. |
| 9,028,492 | B2 | 5/2015 | Kerr et al. |
| 9,033,981 | B2 | 5/2015 | Olson et al. |
| 9,034,009 | B2 | 5/2015 | Twomey et al. |
| 9,039,691 | B2 | 5/2015 | Moua et al. |
| 9,039,704 | B2 | 5/2015 | Joseph |
| 9,039,732 | B2 | 5/2015 | Sims et al. |
| 9,060,780 | B2 | 6/2015 | Twomey et al. |
| 9,072,524 | B2 | 7/2015 | Heard et al. |
| 9,113,882 | B2 | 8/2015 | Twomey et al. |
| 9,113,899 | B2 | 8/2015 | Garrison et al. |
| 9,113,901 | B2 | 8/2015 | Allen, IV et al. |
| 9,113,909 | B2 | 8/2015 | Twomey et al. |
| 9,113,933 | B2 | 8/2015 | Chernova et al. |
| 9,113,934 | B2 | 8/2015 | Chernov et al. |
| 9,113,938 | B2 | 8/2015 | Kerr |
| 9,161,807 | B2 | 10/2015 | Garrison |
| 9,192,432 | B2 | 11/2015 | Larson et al. |
| 9,259,268 | B2 | 2/2016 | Behnke, II et al. |
| 9,265,565 | B2 | 2/2016 | Kerr |
| 9,265,568 | B2 | 2/2016 | Chernov et al. |
| 9,265,569 | B2 | 2/2016 | Hart et al. |
| 9,820,765 | B2 | 11/2017 | Allen, IV et al. |
| 9,861,378 | B2 | 1/2018 | Allen, IV et al. |
| 10,588,651 | B2 | 3/2020 | Allen, IV et al. |
| 2002/0058925 | A1 | 5/2002 | Kaplan et al. |
| 2002/0188294 | A1 | 12/2002 | Couture et al. |
| 2003/0018331 | A1 | 1/2003 | Dycus et al. |
| 2003/0229344 | A1 | 12/2003 | Dycus et al. |
| 2004/0087943 | A1 | 5/2004 | Dycus et al. |
| 2004/0254573 | A1 | 12/2004 | Dycus et al. |
| 2005/0251151 | A1 | 11/2005 | Teague |
| 2008/0077180 | A1 | 3/2008 | Kladakis et al. |
| 2009/0088743 | A1 | 4/2009 | Masuda |
| 2009/0182327 | A1 | 7/2009 | Unger |
| 2009/0209960 | A1 | 8/2009 | Chojin |
| 2010/0082041 | A1 | 4/2010 | Prisco |
| 2010/0094287 | A1 | 4/2010 | Cunningham et al. |
| 2010/0145334 | A1* | 6/2010 | Olson ............... A61B 18/1445 606/51 |
| 2010/0179545 | A1 | 7/2010 | Twomey et al. |
| 2011/0009864 | A1 | 1/2011 | Bucciaglia et al. |
| 2011/0184405 | A1 | 7/2011 | Mueller |
| 2011/0251612 | A1 | 10/2011 | Faller et al. |
| 2011/0301592 | A1 | 12/2011 | Kerr et al. |
| 2011/0301603 | A1 | 12/2011 | Kerr et al. |
| 2012/0226276 | A1 | 9/2012 | Dycus |
| 2012/0239034 | A1 | 9/2012 | Horner et al. |
| 2012/0253344 | A1 | 10/2012 | Dumbauld et al. |
| 2012/0259331 | A1 | 10/2012 | Garrison |
| 2012/0265241 | A1 | 10/2012 | Hart et al. |
| 2012/0283727 | A1 | 11/2012 | Twomey |
| 2012/0283734 | A1 | 11/2012 | Ourada |
| 2012/0296205 | A1 | 11/2012 | Chernov et al. |
| 2012/0296238 | A1 | 11/2012 | Chernov et al. |
| 2012/0296239 | A1 | 11/2012 | Chernov et al. |
| 2012/0296317 | A1 | 11/2012 | Chernov et al. |
| 2012/0296323 | A1 | 11/2012 | Chernov et al. |
| 2012/0296324 | A1 | 11/2012 | Chernov et al. |
| 2012/0296332 | A1 | 11/2012 | Chernov et al. |
| 2012/0296333 | A1 | 11/2012 | Twomey |
| 2012/0296334 | A1 | 11/2012 | Kharin |
| 2012/0296371 | A1 | 11/2012 | Kappus et al. |
| 2012/0303021 | A1 | 11/2012 | Guerra et al. |
| 2012/0303025 | A1 | 11/2012 | Garrison |
| 2012/0303026 | A1 | 11/2012 | Dycus et al. |
| 2012/0310240 | A1 | 12/2012 | Olson et al. |
| 2012/0316601 | A1 | 12/2012 | Twomey |
| 2012/0323238 | A1 | 12/2012 | Tyrrell et al. |
| 2012/0330308 | A1 | 12/2012 | Joseph |
| 2012/0330309 | A1 | 12/2012 | Joseph |
| 2013/0014375 | A1 | 1/2013 | Hempstead et al. |
| 2013/0018364 | A1 | 1/2013 | Chernov et al. |

| | | | |
|---|---|---|---|
| 2013/0018371 | A1 | 1/2013 | Twomey |
| 2013/0018372 | A1 | 1/2013 | Sims et al. |
| 2013/0022495 | A1 | 1/2013 | Allen, IV et al. |
| 2013/0041370 | A1 | 2/2013 | Unger |
| 2013/0041402 | A1 | 2/2013 | Chojin et al. |
| 2013/0046295 | A1 | 2/2013 | Kerr et al. |
| 2013/0046303 | A1 | 2/2013 | Evans et al. |
| 2013/0046306 | A1 | 2/2013 | Evans et al. |
| 2013/0046337 | A1 | 2/2013 | Evans et al. |
| 2013/0060250 | A1 | 3/2013 | Twomey et al. |
| 2013/0066303 | A1 | 3/2013 | Hart |
| 2013/0066318 | A1 | 3/2013 | Kerr |
| 2013/0071282 | A1 | 3/2013 | Fry |
| 2013/0072919 | A1 | 3/2013 | Allen, IV et al. |
| 2013/0072927 | A1 | 3/2013 | Allen, IV et al. |
| 2013/0079760 | A1 | 3/2013 | Twomey et al. |
| 2013/0079762 | A1 | 3/2013 | Twomey et al. |
| 2013/0079774 | A1 | 3/2013 | Whitney et al. |
| 2013/0082035 | A1 | 4/2013 | Allen, IV et al. |
| 2013/0085491 | A1 | 4/2013 | Twomey et al. |
| 2013/0085496 | A1 | 4/2013 | Unger et al. |
| 2013/0085516 | A1 | 4/2013 | Kerr et al. |
| 2013/0103030 | A1 | 4/2013 | Garrison |
| 2013/0103031 | A1 | 4/2013 | Garrison |
| 2013/0103035 | A1 | 4/2013 | Horner et al. |
| 2013/0123837 | A1 | 5/2013 | Roy et al. |
| 2013/0138101 | A1 | 5/2013 | Kerr |
| 2013/0138102 | A1 | 5/2013 | Twomey et al. |
| 2013/0138129 | A1 | 5/2013 | Garrison et al. |
| 2013/0144284 | A1 | 6/2013 | Behnke, II et al. |
| 2013/0150842 | A1 | 6/2013 | Nau, Jr. et al. |
| 2013/0178852 | A1 | 7/2013 | Allen, IV et al. |
| 2013/0185922 | A1 | 7/2013 | Twomey et al. |
| 2013/0190753 | A1 | 7/2013 | Garrison |
| 2013/0190760 | A1 | 7/2013 | Allen, IV |
| 2013/0197503 | A1 | 8/2013 | Orszulak |
| 2013/0218198 | A1 | 8/2013 | Larson |
| 2013/0226177 | A1 | 8/2013 | Brandt |
| 2013/0226178 | A1 | 8/2013 | Brandt et al. |
| 2013/0232753 | A1 | 9/2013 | Ackley |
| 2013/0238016 | A1 | 9/2013 | Garrison |
| 2013/0245623 | A1 | 9/2013 | Twomey |
| 2013/0247343 | A1 | 9/2013 | Horner et al. |
| 2013/0253489 | A1 | 9/2013 | Nau, Jr. et al. |
| 2013/0255063 | A1 | 10/2013 | Hart et al. |
| 2013/0267948 | A1 | 10/2013 | Kerr et al. |
| 2013/0267949 | A1 | 10/2013 | Kerr |
| 2013/0270322 | A1 | 10/2013 | Scheib et al. |
| 2013/0274736 | A1 | 10/2013 | Garrison |
| 2013/0282010 | A1 | 10/2013 | McKenna et al. |
| 2013/0289561 | A1 | 10/2013 | Waaler et al. |
| 2013/0296848 | A1 | 11/2013 | Allen, IV |
| 2013/0296854 | A1 | 11/2013 | Mueller |
| 2013/0296856 | A1 | 11/2013 | Unger et al. |
| 2013/0296922 | A1 | 11/2013 | Allen, IV et al. |
| 2013/0296923 | A1 | 11/2013 | Twomey et al. |
| 2013/0304058 | A1 | 11/2013 | Kendrick |
| 2013/0304059 | A1 | 11/2013 | Allen, IV et al. |
| 2013/0304066 | A1 | 11/2013 | Kerr et al. |
| 2013/0310832 | A1 | 11/2013 | Kerr et al. |
| 2013/0325057 | A1 | 12/2013 | Larson et al. |
| 2013/0331837 | A1 | 12/2013 | Larson |
| 2013/0338666 | A1 | 12/2013 | Bucciaglia et al. |
| 2013/0338693 | A1 | 12/2013 | Kerr et al. |
| 2013/0345701 | A1 | 12/2013 | Allen, IV et al. |
| 2013/0345706 | A1 | 12/2013 | Garrison |
| 2013/0345735 | A1 | 12/2013 | Mueller |
| 2014/0005663 | A1 | 1/2014 | Heard et al. |
| 2014/0005666 | A1 | 1/2014 | Moua et al. |
| 2014/0025052 | A1 | 1/2014 | Nau, Jr. et al. |
| 2014/0025053 | A1 | 1/2014 | Nau, Jr. et al. |
| 2014/0025059 | A1 | 1/2014 | Kerr |
| 2014/0025060 | A1 | 1/2014 | Kerr |
| 2014/0025066 | A1 | 1/2014 | Kerr |
| 2014/0025067 | A1 | 1/2014 | Kerr et al. |

(56) References Cited

U.S. PATENT DOCUMENTS

| | | | |
|---|---|---|---|
| 2014/0025070 A1 | 1/2014 | Kerr et al. | |
| 2014/0025073 A1 | 1/2014 | Twomey et al. | |

FOREIGN PATENT DOCUMENTS

| | | | |
|---|---|---|---|
| DE | 2415263 | A1 | 10/1975 |
| DE | 02514501 | A1 | 10/1976 |
| DE | 2627679 | A1 | 1/1977 |
| DE | 03423356 | C2 | 6/1986 |
| DE | 03612646 | A1 | 4/1987 |
| DE | 8712328 | U1 | 2/1988 |
| DE | 04303882 | C2 | 2/1995 |
| DE | 04403252 | A1 | 8/1995 |
| DE | 19515914 | C1 | 7/1996 |
| DE | 19506363 | A1 | 8/1996 |
| DE | 19616210 | U1 | 11/1996 |
| DE | 19608716 | C1 | 4/1997 |
| DE | 19751106 | A1 | 5/1998 |
| DE | 19738457 | A1 | 3/1999 |
| DE | 19751108 | A1 | 5/1999 |
| DE | 19946527 | C1 | 7/2001 |
| DE | 20121161 | U1 | 4/2002 |
| DE | 10045375 | C2 | 10/2002 |
| DE | 202007009165 | U1 | 8/2007 |
| DE | 202007009317 | U1 | 8/2007 |
| DE | 202007009318 | U1 | 8/2007 |
| DE | 110031773 | B4 | 11/2007 |
| DE | 202007016233 | U1 | 1/2008 |
| DE | 102004026179 | B4 | 1/2009 |
| DE | 102008018406 | B3 | 7/2009 |
| EP | 0584787 | A1 | 3/1994 |
| EP | 1159926 | A2 | 3/2003 |
| EP | 1535581 | A2 | 6/2005 |
| EP | 1810625 | A1 | 7/2007 |
| EP | 2294998 | A1 | 3/2011 |
| EP | 2347725 | A1 | 7/2011 |
| JP | 61501068 | A | 5/1986 |
| JP | 1024051 | | 1/1989 |
| JP | 1147150 | | 6/1989 |
| JP | 55106 | | 1/1993 |
| JP | 0540112 | A | 2/1993 |
| JP | 6121797 | A | 5/1994 |
| JP | 6285078 | A | 10/1994 |
| JP | 06343644 | | 12/1994 |
| JP | 6511401 | | 12/1994 |
| JP | 07265328 | | 10/1995 |
| JP | 855955 | | 5/1996 |
| JP | 08252263 | A | 10/1996 |
| JP | 8289895 | A | 11/1996 |
| JP | 8317934 | A | 12/1996 |
| JP | 8317935 | A | 12/1996 |
| JP | H08317936 | A | 12/1996 |
| JP | 910223 | A | 1/1997 |
| JP | 9122138 | A | 5/1997 |
| JP | 0010000195 | A | 1/1998 |
| JP | 10155798 | A | 6/1998 |
| JP | 11070124 | A | 3/1999 |
| JP | 11169381 | A | 6/1999 |
| JP | 11192238 | A | 7/1999 |
| JP | 11244298 | A | 9/1999 |
| JP | 2000102545 | A | 4/2000 |
| JP | 2000342599 | A | 12/2000 |
| JP | 2000350732 | A | 12/2000 |
| JP | 2001003400 | A | 1/2001 |
| JP | 2001008944 | A | 1/2001 |
| JP | 2001128990 | A | 5/2001 |
| JP | 2001190564 | A | 7/2001 |
| JP | 2002136525 | A | 5/2002 |
| JP | 2002528166 | A | 9/2002 |
| JP | 2003175052 | A | 6/2003 |
| JP | 2003245285 | A | 9/2003 |
| JP | 2004517668 | A | 6/2004 |
| JP | 2004528869 | A | 9/2004 |
| JP | 2005253789 | A | 9/2005 |
| JP | 2006015078 | A | 1/2006 |
| JP | 2006501939 | A | 1/2006 |
| JP | 2006095316 | A | 4/2006 |
| JP | 2009240781 | A | 10/2009 |
| JP | 2011125195 | A | 6/2011 |
| JP | 0006030945 | B2 | 11/2016 |
| JP | 6502328 | B2 | 4/2019 |
| SU | 401367 | A1 | 10/1973 |
| WO | 0036986 | A1 | 6/2000 |
| WO | 0059392 | A1 | 10/2000 |
| WO | 0115614 | A1 | 3/2001 |
| WO | 0154604 | A1 | 8/2001 |
| WO | 0245589 | A2 | 6/2002 |
| WO | 2005110264 | A2 | 4/2006 |
| WO | 2006083728 | A2 | 8/2006 |
| WO | 2010014825 | A1 | 2/2010 |
| WO | 2010114634 | A1 | 10/2010 |

OTHER PUBLICATIONS

European Examination Report issued in Appl. No. 13166214.0 dated Nov. 2, 2017.

Canadian Office Action issued in corresponding Appl. No. CA 2,813,637 dated Mar. 6, 2019 (4 pages).

Second Chinese Office Action and English language translation issued in application No. 201310153890.5 dated Oct. 28, 2016.

Japanese Office Action from Appl. No. 2013-95176 dated Sep. 14, 2016.

Michael Cheli, "Abdominoperineal Resection with the LigaSure Vessel Sealing System and LigaSure Atlas 20 cm Open Instrument" Innovations That Work, Jun. 2003.

Chung et al., "Clinical Experience of Sutureless Closed Hemonloidectomy with LigaSure"; Diseases of the Colon & Rectum vol. 46, No. Jan. 1, 2003.

Tinkcler L.F., "Combined Diathermy and Suction Forceps", Feb. 6, 1967 {Feb. 6, 1965), British Medical Journal Feb. 6, 1976, vol. 1, nr. 5431 p. 361, ISSN: 0007-1447.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlolle, NC; Date: Aug. 2003.

Peterson et al., "Comparison of Healing Process Following Ligation with Sutures and Bipolar Vessel Sealing" Surgical Technology International (2001).

Johnson et al. "Evaluation of a Bipolar Electrothermal Vessel Sealing Device in Hemorrhoidectomy" Sales/Product Literature; Jan. 2004.

E. David Crawford, "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al. "Extended Left Hemicolectomy Using the LigaSure Vessel Sealing System" Innovations That Work; Sep. 1999.

Kennedy et al. "High-burst-strength, feedback-controlled bipolar vessel sealing" Surgical Endoscopy (1998) 12:876-878.

Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 114-427.

Carus et al., "Initial Experience With the LigaSure Vessel Sealing System in Abdominal Surgery" Innovations That Nork.Jun. 2002.

Heniford et al. "Initial Research and Clinical Results with an Electrothermal Bipolar Vessel Sealer" Oct. 1999.

Heniford et al "Initial Results with an Electrothermal Bipolar Vessel Sealer" Surgical Endoscopy (2000) 15:799-801.

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

(56)            References Cited

OTHER PUBLICATIONS

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparaoscopic Surgery; Sales/Product Literature; Apr. 2002.

Joseph Ortenberg "LigaSure System Used in Laparoscopic 1st and 2nd Stage Orchiopexy" Innovations That Work, Nov. 2002.

Sigel et al., "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery ,01. 181, No. 3, Apr. 2001 pp. 236-237.

Benaron et al., "Optical Time-Of-Flight and Absorbance Imaging of Biologic Media", American Association for the Advancement of Science, Washington, DC, vol. 259, Mar. 5, 1993, pp. 1463-1466.

Olsson et al. "Radical Cystectomy in Females" . Current Surgical Techniques in Urology, vol. 14, Issue 3, 2001.

Palazzo et al. "Randomized clinical trial of Ligasure versus open haemorrhoidectomy" British Journal of Surgery 2002, 89, 154-157.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

Reducing Needlestick Injuries in the Operating Room; Sales/Product Literature 2001.

Bergdahl et al., "Studies on Coagulation and the Development of an Automatic Computerized Bipolar Coagulator" J. Neurosurg, vol. 75, Jul. 1991, pp. 148-151.

Strasberg et al. "A Phase I Study of the LigaSure Vessel Sealing System in Hepatic Surgery" Section of HPB Surger, Nashington University School of Medicine, SI. Louis MO, Presented at AH-PBA , Feb. 2001.

Sayfan et al., "Sutureless Closed Hemorrhoidectomy: A New Technique" Annals of Surgery, vol. 234, No. 1, Jul. 2001, Jp. 21-24.

Levy et al., "Update on Hysterectomy-New Technologies and Techniques" OBG Management, Feb. 2003.

Dulemba et al. "Use of a Bipolar Electrothermal Vessel Sealer in Laparoscopically Assisted Vaginal Hysterectomy" Sales/Product Literature; Jan. 2004.

Strasberg et al., "Use of a Bipolar Vessel-Sealing Device for Parenchymal Transection During Liver Surgery" Journal Jf Gastrointestinal Surgery, vol. 6, No. 4, Jul./Aug. 2002 pp. 569-574.

Sengupta et al., "Use of a Computer-Controlled Bipolar Diathermy System in Radical Prostatectomies and Other Open Urological Surgery" ANZ Journal of Surgery (2001)71.9 pp. 538-540.

Rothenberg et al. "Use of the LigaSure Vessel Sealing System in Minimally Invasive Surgery in Children" Int'l Pediatric Endosurgery Group {IPEG) 2000.

Cawford et al. "Use of the LigaSure Vessel Sealing System in Urologic Cancer Surgery"; Grand Rounds in Urology 1999 vol. 1 Issue 4 pp. 10-17.

Craig Johnson, "Use of the LigaSure Vessel Sealing System in Bloodless Hemorrhoidectomy"; Innovations That Work, Mar. 2000.

Levy et al. "Use of a New Energy-based Vessel Ligation Device During Vaginal Hysterectomy"; Int'l Federation of Gynecology and Obstetrics {FIGO) World Congress 1999.

Barbara Levy, "Use of a New Vessel Ligation Device During Vaginal Hysterectomy" FIGO 2000, Washington, D.C.

E. David Crawford, "Use of a Novel Vessel Sealing Technology in Management of the Dorsal Veinous Complex" Sales Product Literature 2000.

Jarrett et al., "Use of the LigaSure Vessel Sealing System for Peri-Hilar Vessels in Laparoscopic Nephrectomy"; Sales/Product Literature 2000.

Crouch et al. "A Velocity-Dependent Model for Needle Insertion in Soft Tissue"; MICCAI 2005; NCS 3750 pp. 624-632, Dated: 2005.

Mclellan et al., "Vessel Sealing for Hemostasis During Pelvic Surgery" Int'l Federation of Gynecology and Obstetrics FIGO World Congress 2000, Washington, DC.

Mclellan et al. Vessel Sealing for Hemostasis During Gynecologic Surgery Sales/Product Literature 1999.

Chinese Office Action issued in corresponding application No. 201310154366.X dated Feb. 1, 2016.

Chinese office action and English language translation issued in application No. 201310153890.5 dated Mar. 2016.

Australian Examination Report No. 1 issued in Appl. No. AU 2015204316 dated Jan. 18, 2017.

* cited by examiner

SURGICAL INSTRUMENT FOR TREATING TISSUE

CROSS-REFERENCE TO RELATED APPLICATIONS

This application is a continuation of U.S. patent application Ser. No. 16/817,935, filed on Mar. 13, 2020, which is a continuation of U.S. patent application Ser. No. 15/844,821, filed on Dec. 18, 2017, now U.S. Pat. No. 10,588,651, which is a continuation of U.S. patent application Ser. No. 15/013, 096, filed on Feb. 2, 2016, now U.S. Pat. No. 9,861,378, which is a divisional of U.S. patent application Ser. No. 13/461,335, filed on May 1, 2012, now U.S. Pat. No. 9,820,765.

INTRODUCTION

The present disclosure relates generally to the field of surgical instruments. In particular, the disclosure relates to an endoscopic electrosurgical forceps that is economical to manufacture and is capable of sealing and cutting relatively large tissue structures.

BACKGROUND

Instruments such as electrosurgical forceps are commonly used in open and endoscopic surgical procedures to coagulate, cauterize and seal tissue. Such forceps typically include a pair of jaws that can be controlled by a surgeon to grasp targeted tissue, such as, e.g., a blood vessel. The jaws may be approximated to apply a mechanical clamping force to the tissue, and are associated with at least one electrode to permit the delivery of electrosurgical energy to the tissue. The combination of the mechanical clamping force and the electrosurgical energy has been demonstrated to join adjacent layers of tissue captured between the jaws. When the adjacent layers of tissue include the walls of a blood vessel, sealing the tissue may result in hemostasis, which may facilitate the transection of the sealed tissue. A detailed discussion of the use of an electrosurgical forceps may be found in U.S. Pat. No. 7,255,697 to Dycus et al.

A bipolar electrosurgical forceps typically includes opposed electrodes disposed on clamping faces of the jaws. The electrodes are charged to opposite electrical potentials such that an electrosurgical current may be selectively transferred through tissue grasped between the electrodes. To effect a proper seal, particularly in relatively large vessels, two predominant mechanical parameters must be accurately controlled; the pressure applied to the vessel, and the gap distance established between the electrodes.

Both the pressure and gap distance influence the effectiveness of the resultant tissue seal. If an adequate gap distance is not maintained, there is a possibility that the opposed electrodes will contact one another, which may cause a short circuit and prevent energy from being transferred through the tissue. Also, if too low a force is applied the tissue may have a tendency to move before an adequate seal can be generated. The thickness of a typical effective tissue seal is optimally between about 0.001 and about 0.006 inches. Below this range, the seal may shred or tear and above this range the vessel walls may not be effectively joined. Closure pressures for sealing large tissue structures preferably fall within the range of about 3 kg/cm2 to about 16 kg/cm2.

As is traditional, the term "distal" refers herein to an end of the apparatus that is farther from an operator, and the term "proximal" refers herein to the end of the electrosurgical forceps that is closer to the operator.

SUMMARY

The present disclosure relates to an electrosurgical apparatus and methods for performing electrosurgical procedures. More particularly, the present disclosure relates to electrosurgically sealing tissue.

The present disclosure describes a surgical instrument for treating tissue that is economical to manufacture and is capable of sealing and cutting relatively large tissue structures.

The surgical instrument includes an elongated shaft having a distal portion and a proximal portion coupled to a housing. The elongated shaft defines a longitudinal axis. An inner shaft member extends at least partially through the elongated shaft. The inner shaft member is selectively movable in a longitudinal direction with respect to the elongated shaft. An end effector adapted for treating tissue is supported by the distal portion of the elongated shaft. The end effector includes upper and lower jaw members pivotally coupled to the distal portion of the elongated shaft about a pivot axis. The upper and lower jaw members include a first and second pair of laterally spaced flanges, respectively. The first and second pairs of flanges of the jaw members are arranged in an offset configuration such that one flange of the upper jaw member is positioned on a laterally exterior side of a corresponding flange of the lower jaw member, and the other flange of the upper jaw member is positioned on a laterally interior side of the other flange of the lower jaw member.

Additionally or alternatively, the housing includes a movable actuating mechanism configured to cause longitudinal movement of the inner shaft member relative to the elongated shaft.

Additionally or alternatively, the elongated shaft includes at least one feature formed therein configured to operably engage the movable actuating mechanism.

Additionally or alternatively, the elongated shaft has a generally circular profile joined along two opposing longitudinal edges.

Additionally or alternatively, the two opposing longitudinal edges are laser welded together.

Additionally or alternatively, the two opposing longitudinal edges are joined by one of a box joint interface and a dovetail joint interface.

Additionally or alternatively, the surgical instrument includes a cam pin supported by the inner shaft member such that longitudinal movement of the inner shaft member is imparted to the cam pin.

Additionally or alternatively, each of the first and second laterally spaced flanges define a camming slot for engaging the cam pin.

Additionally or alternatively, the upper and lower jaw members are constructed as substantially identical components positioned in a laterally offset manner with respect to one another.

Additionally or alternatively, the pivot axis extends through each of the flanges in a direction substantially transverse to the longitudinal axis.

Additionally or alternatively, the inner shaft member extends through the jaw members on a laterally interior side of each of the flanges.

Additionally or alternatively, the surgical instrument includes a knife selectively movable in a longitudinal direction with respect to the inner shaft member.

Additionally or alternatively, the inner shaft member includes a knife guide disposed on a distal end of the inner shaft member such that the knife is substantially surrounded on four lateral sides.

According to another aspect of the present disclosure, a surgical instrument is provided. The surgical instrument includes an elongated shaft including a distal portion and a proximal portion coupled to a housing. The elongated shaft defines a longitudinal axis. An end effector adapted for treating tissue is supported by the distal portion of the elongated shaft. The end effector includes first and second jaw members pivotally coupled to one another to move between open and closed configurations. Each of the jaw members includes a pair of laterally spaced flanges. Each of the flanges includes a camming surface. A knife extends at least partially through the elongated shaft and is selectively movable in a longitudinal direction between the flanges of the jaw members. A blade of the knife is extendable into a tissue contacting portion of the jaw members. An inner shaft member extends at least partially through the elongated shaft and is selectively movable in a longitudinal direction with respect to the knife and with respect to the elongated shaft. The inner shaft member carries a cam pin positioned to engage the camming surface of each of the flanges to induce the jaw members to move between the open and closed configurations.

Additionally or alternatively, the elongated shaft includes at least one feature defined therein configured to engage a movable actuating mechanism operably associated with the housing.

Additionally or alternatively, the laterally spaced flanges of the jaw members are arranged in a nestled configuration wherein both of the flanges of one of the jaw members are arranged within a laterally interior side of the laterally spaced flanges of the other of the jaw members.

According to another aspect of the present disclosure, a method of manufacturing a surgical device including a housing and an elongated shaft for coupling an end effector with the housing of the surgical device is provided. The method includes the steps of stamping at least one feature into a blank of sheet metal and folding the blank into such that two opposing longitudinal edges of the blank meet at a longitudinal seam to form an elongated shaft. The method also includes the step of operably coupling an end effector to at least one feature formed at a distal portion of the elongated shaft. The method also includes the step of engaging at least one actuating mechanism supported by a housing with at least one feature formed at a proximal portion of the elongated shaft to operably couple the proximal portion of the elongated shaft with the housing. The actuating mechanism is configured to selectively move the end effector between an open position and a closed position.

Additionally or alternatively, the method includes the step of joining the two opposing longitudinal edges along the longitudinal seam.

Additionally or alternatively, the joining step further comprises laser welding the longitudinal seam. The longitudinal seam may be a box joint configuration or a dovetail joint configuration.

Additionally or alternatively, the method includes the step of coupling a drive rod to the at least one actuating mechanism at a proximal end and to the end effector at a distal end. The drive rod may be configured to translate within and relative to the elongated shaft upon movement of the at least one actuation mechanism to effect actuation of the end effector.

Additionally or alternatively, the method includes the step of stamping at least one feature at a distal end of the blank such that a clevis is formed at a distal end of the elongated shaft. The clevis may be configured to support the end effector.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION

Figure 1:
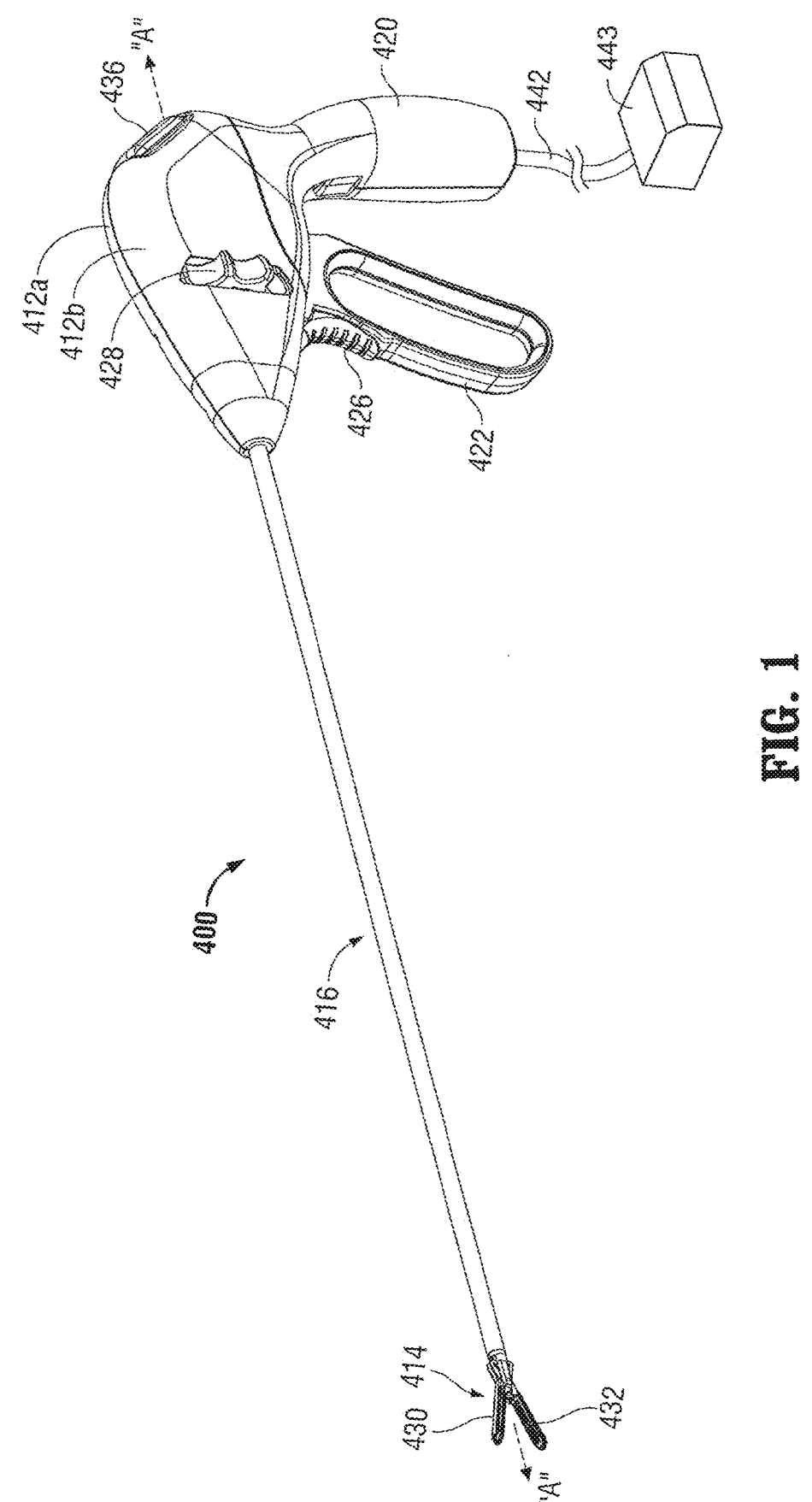
FIG. 1 is a perspective view of an electrosurgical forceps according to an embodiment of the present disclosure including a housing, an elongated shaft, and an end effector.

Referring initially to FIG. 1, an embodiment of an electrosurgical forceps 400 generally includes a housing 412 that supports various actuators thereon for remotely controlling an end effector 414 through an elongated shaft 416. Although this configuration is typically associated with instruments for use in laparoscopic or endoscopic surgical procedures, various aspects of the present disclosure may be practiced with traditional open instruments and in connection with endoluminal procedures as well.

The housing 412 is constructed of a left housing half 412*a* and a right housing half 412*b*. The left and right designation of the housing halves 412*a*, 412*b* refer to the respective directions as perceived by an operator using the forceps 400. The housing halves 412*a*, 412*b* may be constructed of sturdy plastic, and may be joined to one another by adhesives, ultrasonic welding or other suitable assembly methods.

To mechanically control the end effector 414, the housing 412 supports a stationary handle 420, a movable handle 422, a trigger 426 and a rotation knob 428. The movable handle 422 is operable to move the end effector 414 between an open configuration (FIG. 2A) wherein a pair of opposed jaw members 430, 432 are disposed in spaced relation relative to one another, and a closed or clamping configuration (FIG. 2B) wherein the jaw members 430, 432 are closer together. Approximation of the movable handle 422 with the stationary handle 420 serves to move the end effector 414 to the closed configuration and separation of the movable handle 422 from the stationary handle 420 serves to move the end effector 414 to the open configuration. The trigger 426 is operable to extend and retract a knife blade 456 (see FIGS. 2A and 2B) through the end effector 414 when the end effector 414 is in the closed configuration. The rotation knob 428 serves to rotate the elongated shaft 416 and the end effector 414 about a longitudinal axis A-A extending through the forceps.

To electrically control the end effector 414, the housing 412 supports a switch 436 thereon, which is operable by the user to initiate and terminate the delivery of electrosurgical energy to the end effector 414. The switch 436 is in electrical communication with a source of electrosurgical energy such as electrosurgical generator 443 or a battery (not shown) supported within the housing 412. The generator 443 may include devices such as the LIGASURE® Vessel Sealing Generator and the Force Triad® Generator as sold by Covidien Energy-based Devices of Boulder, Colorado. A cable 442 extends between the housing 412 and the generator 443 and may include a connector (not shown) thereon such that the forceps 400 may be selectively coupled and decoupled electrically from the generator 443.

Figure 2A:
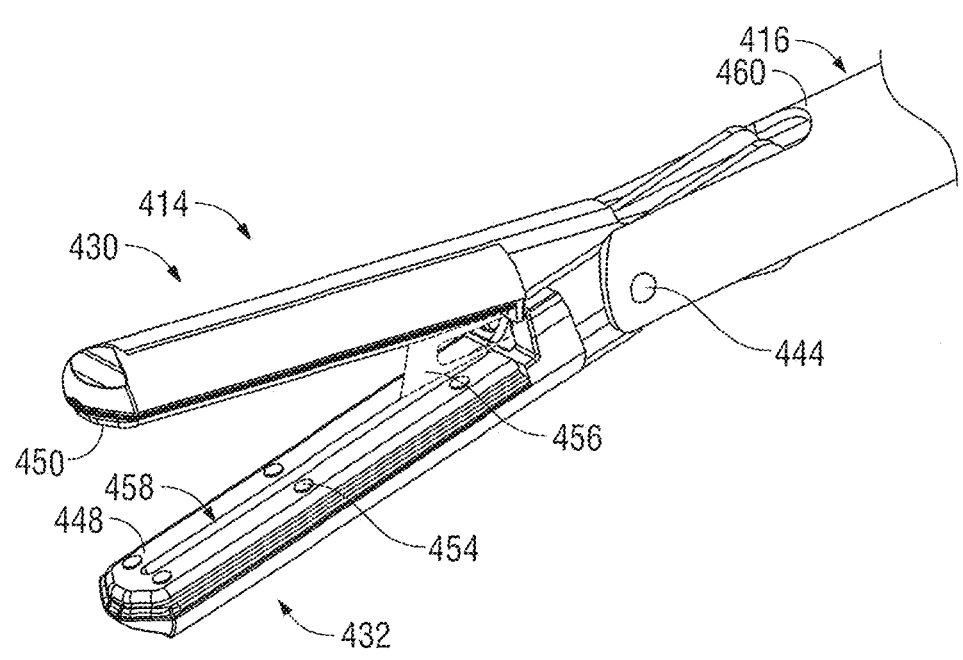
FIG. 2A is an enlarged perspective view of the end effector of FIG. 1 depicted with a pair of jaw members in an open configuration.
Figure 2B:
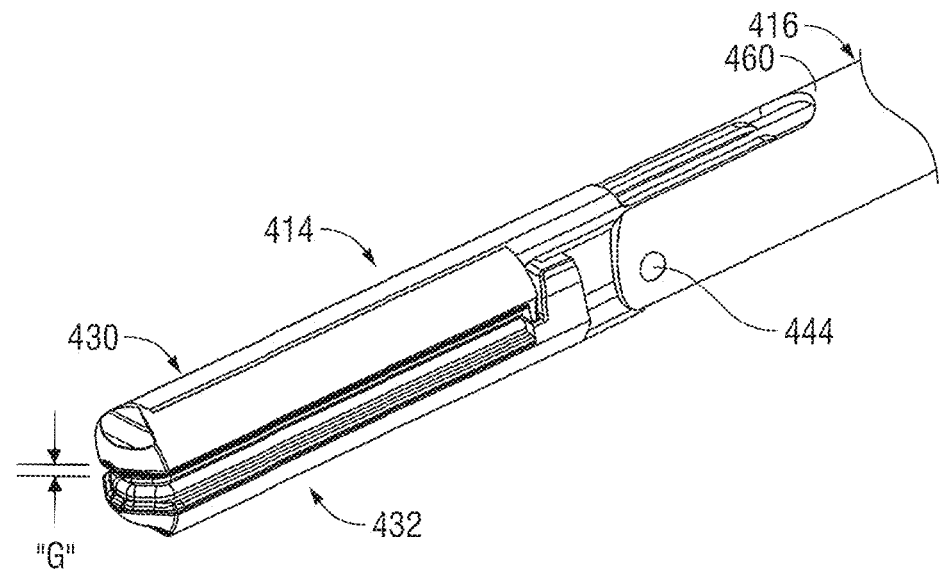
FIG. 2B is an enlarged perspective view of the end effector of FIG. 1 depicted with the pair of jaw members in a closed configuration.

Referring now to FIGS. 2A-3, the end effector 414 may be moved from the open configuration (FIG. 2A) wherein tissue (not shown) is received between the jaw members 430, 432, and the closed configuration (FIG. 2B), wherein the tissue is clamped and sealed. Upper jaw member 430 and lower jaw member 432 are mechanically coupled to the elongated shaft 416 about a pivot pin 444. The upper and lower jaw members 430, 432 are electrically coupled to cable 442, and thus to the generator 443 (e.g., via a respective wire extending through the elongated shaft 416) to provide an electrical pathway to a pair of electrically conductive, tissue-engaging sealing plates 448, 450 disposed on the lower and upper jaw members 432, 430, respectively. A pair of wire conduits 478*a* and 478*b* may be provided to guide wires proximally from the end effector 414. The wire conduits 478*a* and 478*b* may be constructed of a plastic tube, and serve to protect wires from sharp edges that may form on surrounding components. The sealing plate 448 of the lower jaw member 432 opposes the sealing plate 450 of the upper jaw member 430, and, in some embodiments, the sealing plates 448 and 450 are electrically coupled to opposite terminals, e.g., positive or active (+) and negative or return (−) terminals associated with the generator 443. Thus, bipolar energy may be provided through the sealing plates 448 and 450. Alternatively, the scaling plates 448 and 450 and/or the end effector 414 may be configured for delivering monopolar energy to the tissue. In a monopolar configuration, the one or both sealing plates 448 and 450 deliver electrosurgical energy from an active terminal, e.g. (+), while a return pad (not shown) is placed generally on a patient and provides a return path to the opposite terminal, e.g. (−), of the generator 443.

The jaw members 430, 432 may be pivoted about the pivot pin 444 to move the end effector 414 to the closed configuration of FIG. 2B wherein the sealing plates 448, 450 provide a pressure to tissue grasped therebetween. In some embodiments, to provide an effective seal, a pressure within a range between about 3 kg/cm2 to about 16 kg/cm2 and, desirably, within a working range of 7 kg/cm2 to 13 kg/cm2 is applied to the tissue. Also, in the closed configuration, a separation or gap distance "G" may be maintained between the sealing plates 448, 450 by an array of stop members 454 (FIG. 2A) disposed on or adjacent the scaling plates 448, 450. The stop members 454 contact opposing surfaces on the opposing jaw member 430, 432 and prohibit further approximation of the scaling plates 448, 450. In some embodiments, to provide an effective tissue seal, an appropriate gap distance of about 0.001 inches to about 0.010 inches and, desirably, between about 0.002 and about 0.005 inches may be provided. In some embodiments, the stop members 454 are constructed of an electrically non-conductive plastic or other material molded onto the jaw members 430, 432, e.g., by a process such as overmolding or injection molding. In other embodiments, the stop members 454 are constructed of a heat-resistant ceramic deposited onto the jaw members 430, 432. Other methods of controlling gap are contemplated including those described in the commonly assigned patent application entitled GAP CONTROL VIA OVERMOLD TEETH AND HARD STOPS (application Ser. No. 13/835,004 filed Mar. 15, 2013, now U.S. Pat. No. 8,939, 975).

Electrosurgical energy may be delivered to the tissue through the electrically conductive seal plates 448, 450 to effect a tissue seal. Once a tissue seal is established, a knife blade 456 may be advanced through a knife channel 458 defined in one or both jaw members 430, 432 to transect the sealed tissue. Knife blade 456 is depicted in FIG. 2A as extending from the elongated shaft 416 when the end effector 414 is in an open configuration. In some embodiments, a knife lockout is provided to prevent extension of the knife blade 456 into the knife channel 458 when the end effector 414 is in the open configuration, thus preventing accidental or premature transection of tissue and avoiding safety concerns.

Figure 3A:
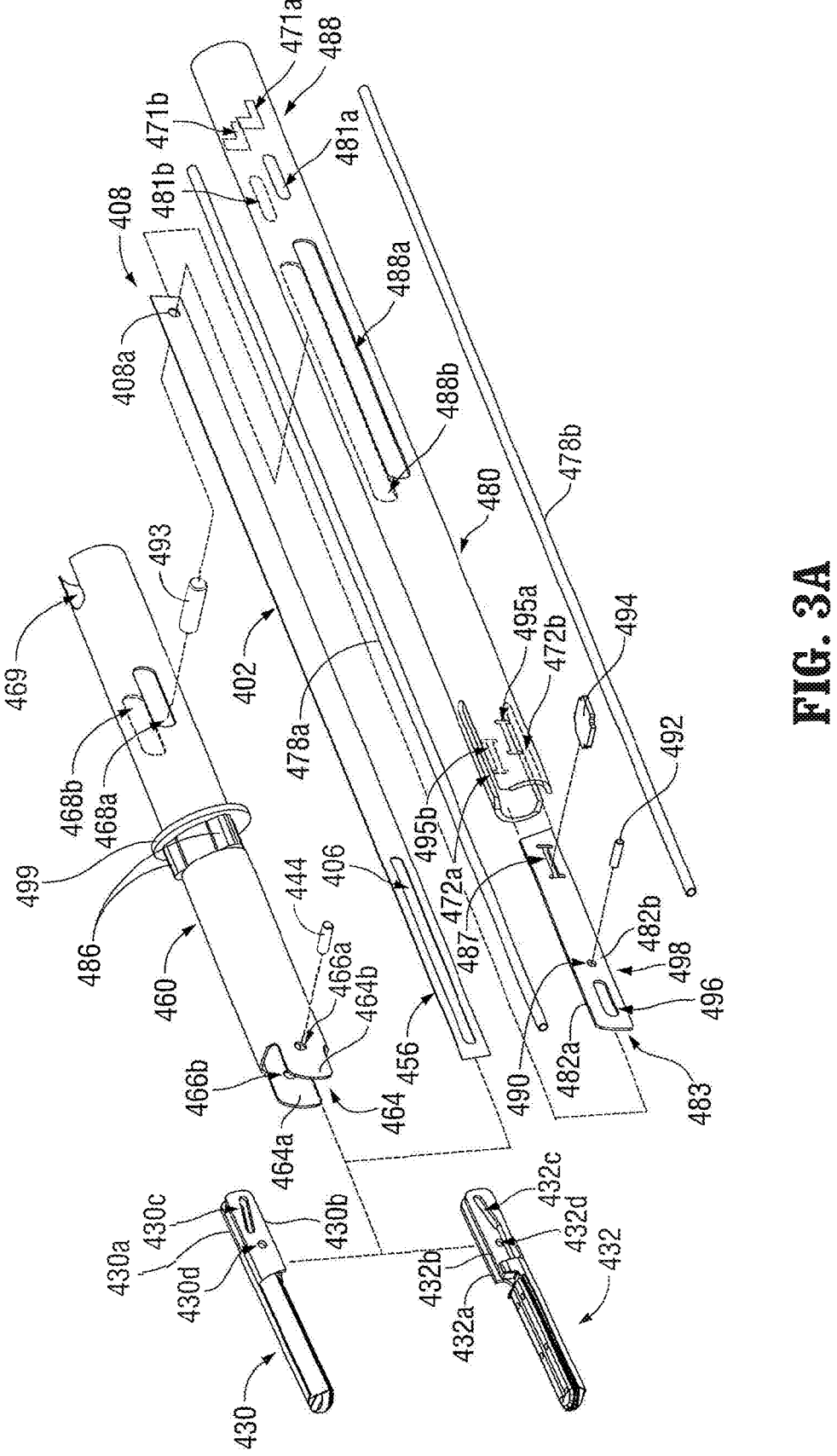
FIG. 3A is a perspective view of the end effector and elongated shaft of FIG. 1 with parts separated.

Referring now to FIG. 3A, the elongated shaft 416 includes various longitudinal components that operatively couple the end effector 414 to the various actuators supported by the housing 412 (FIG. 1). An outer shaft member 460 defines an exterior surface of the elongated shaft 416 and supports movement of other components therethrough as described below. The outer shaft member 460 may be constructed from a flat stock piece of metal. In constructing the outer shaft member 460, a stamping, punching or similar metal-working process may be employed to initially generate a flat blank that includes an appropriate outer profile and any interior openings or features. Thereafter, the necessary bends and curves may be formed by bending the flat blank with a press brake, or other suitable metal-working equipment. The outer shaft member 460 may be formed by folding the flat blank into a generally circular profile (or generally rectangular profile) such that two opposing longitudinal edges of the flat blank meet at a longitudinal scam (not explicitly shown). Although the longitudinal seam does not necessarily require joining by a mechanical interlock or any other suitable process, the scam may, in some embodiments, be joined by laser welding (or other suitable process) to form a continuous circular or other geometric (e.g., rectangular) profile. The scam may be generally straight, or alternatively, a box joint, a dovetail joint, or any other suitable interface known in the metal-working arts.

The outer shaft member 460 defines a clevis 464 at a distal end thereof for receiving the jaw members 430 and 432. Opposing vertical sidewalls 464a and 464b of the outer shaft member 460 include respective bores 466a, 466b extending therethrough to frictionally support the pivot pin 444 and maintain an orientation of the pivot pin 444 with respect to the outer shaft member 460. Alternatively or additionally, the pivot pin 444 may be fastened to the outer shaft member 460 by a laser or heat-based welding, adhesives, chemical bonding, or other suitable manufacturing processes.

At a proximal portion of the outer shaft member 460, various features are provided that serve to couple the outer shaft member 460 to various elements of the housing 412. More specifically, the proximal portion of the outer shaft member 460 includes, in order from distal to proximal, a series of tabs 486 extending therefrom, a washer 499 extending around outer shaft member 460, a pair of opposing longitudinal slots 468a, 468b defined therethrough and provided to allow longitudinal translation of a dowel pin 493 therethrough, and a longitudinal slot 469 extending distally from a proximal end thereof to couple the outer shaft member 460 to the rotation knob 428. The connection established between the outer shaft member 460 and the rotation knob 428 is described below with reference to FIG. 4. As shown in FIGS. 15A-15D, the series of tabs 486 and the washer 499 serve to aid in securing the proximal portion of the outer shaft member 460 within the housing 412.

Figures 8, 9, 10, 11:
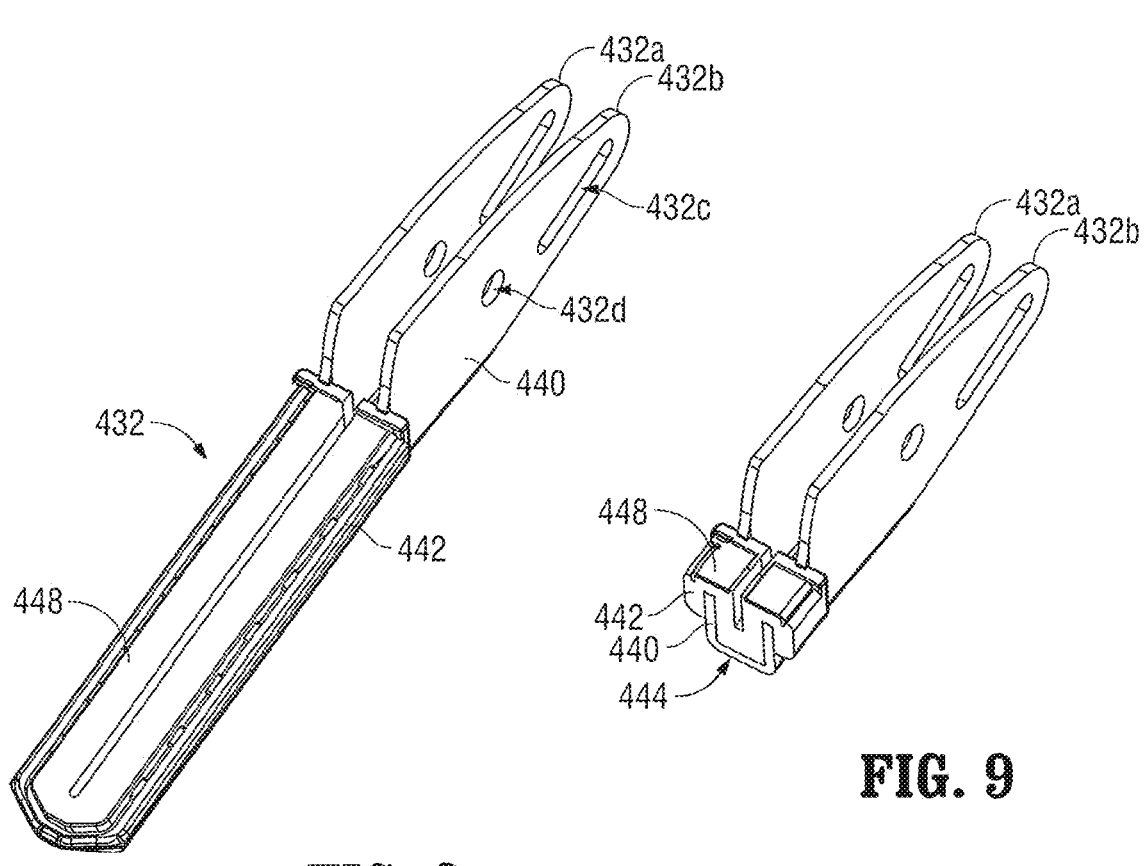
FIG. 8 is a perspective view of a lower jaw member of the end effector of FIG. 1 depicting a double flag at a proximal end thereof.
FIG. 9 is a cross-sectional, perspective view of the lower jaw member of FIG. 8.
FIG. 10 is a schematic view of the nestled arrangement of the double flag of FIG. 8 with a double flag of an upper jaw member.
FIG. 11 is a schematic view of an alternative offset arrangement of double flags of an alternate pair of jaw members.

The pivot pin 444 extends through a proximal portion of each of the jaw members 430, 432 to pivotally support the jaw members 430, 432 at the distal end of the outer shaft member 460. With reference to FIG. 8, a proximal portion of each of the jaw members 430, 432 is configured as a "double flag." The double flag configuration refers to the two laterally spaced parallel flanges or "flags" 430a, 430b and 432a, 432b respectively, extending proximally from a distal portion of the jaw members 430 and 432. A lateral cam slot 430c and a lateral pivot bore 430d extend through each of the flags 430a, 430b of the upper jaw member 430. Similarly, a lateral cam slot 432c and a lateral pivot bore 432d extend through each of the flags 432a, 432b of the lower jaw member 432. The pivot bores 430d, 432d receive the pivot pin 444 in a slip-fit relation that permits the jaw members 430, 432 to pivot about the pivot pin 444 to move the end effector 414 between the open and closed configurations (FIGS. 2A and 2B, respectively).

Figure 3B:
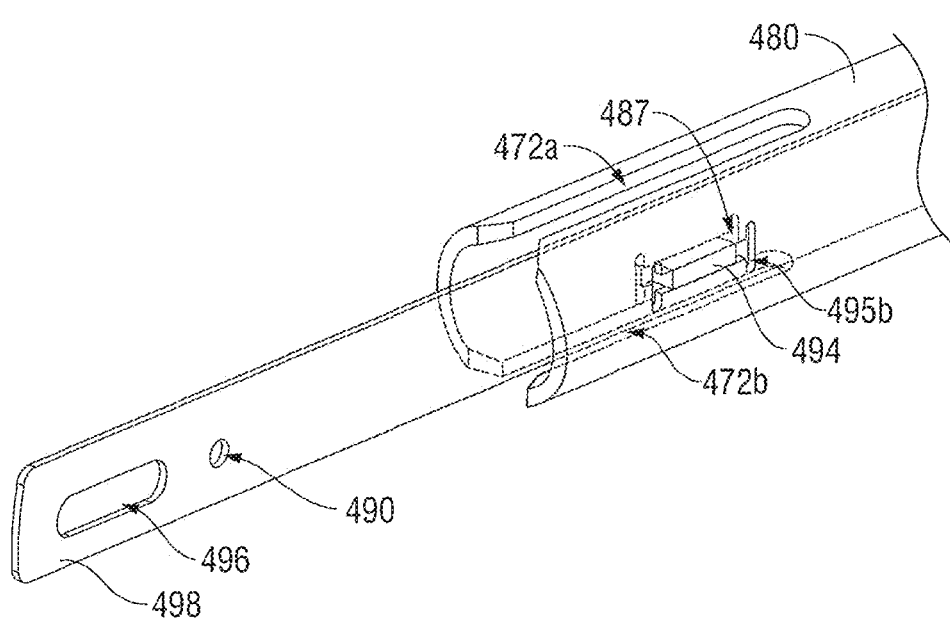
FIG. 3B is an enlarged perspective view of a distal portion of the electrosurgical forceps of FIG. 1 depicting a distal knife guide coupled to an inner shaft member.

An inner shaft member 480 is received within the outer shaft member 460 and is configured for longitudinal motion with respect to the outer shaft member 460. A distal knife guide 498 includes sidewalls 482a, 482b and a proximal key slot 487 that supports a key member 494 therethrough. During assembly of electrosurgical forceps 400, the distal knife guide 498 is slid proximally within a distal end of the inner shaft member 480, such that the inner shaft member 480 surrounds a portion of the distal knife guide 498, and opposing lateral sides of the key member 494 align with and fit within opposing longitudinal key slots 495a, 495b defined through the inner shaft member 480 to couple the knife guide 498 to the inner shaft member 480 (FIG. 3B). The inner shaft member 480 includes a pair of opposing longitudinal slots 472a, 472b extending proximally from a distal end of the inner shaft member 480 along a portion of the inner shaft member 480 between the opposing longitudinal key slots 495a, 495b. The longitudinal slots 472a, 472b allow the distal end of the inner shaft member 480 to aid in sliding of the distal knife guide 498 proximally within the inner shaft member 480. Once the key member 494 is aligned with and fit within the longitudinal key slots 495a, 495b, the key member 494 effectively couples the distal knife guide 498 to the inner shaft member 480, as depicted by FIG. 3B.

The sidewalls 482a, 482b define a longitudinal slot 483 through the distal knife guide 498 that provides lateral support to the knife 402. The knife 402 is substantially surrounded at a distal end thereof by the distal knife guide 498 on four lateral sides and the sidewalls 482a, 482b of the distal knife guide 498 constrain side-to-side lateral motion of the knife 402. Thus, the distal knife guide 498 serves to urge the knife 402 into a central position within the elongated shaft 416, thereby ensuring proper alignment of the knife 402 as the knife 402 reciprocates within knife channel 458 (FIG. 2A). The distal knife guide 498 includes features for operatively coupling the inner shaft member 480 to the end effector 414. A proximal portion 488 of the inner shaft member 480 is configured for receipt within the housing 412 (FIG. 1), and includes features for operatively coupling the inner shaft member 480 to the actuators supported thereon, e.g. the movable handle 422.

The distal knife guide 498 includes a through bore 490 extending through the sidewalls 482a, 482b for receiving the cam pin 492. Distally of the through bore 490, a longitudinal slot 496 is defined through the sidewalls 482a, 482b. The longitudinal slot 496 provides clearance for the pivot pin 444, and thus, permits longitudinal reciprocation of the inner shaft member 480 independent of the pivot pin 444.

The proximal portion 488 of the inner shaft member 480 includes, in order from distal to proximal, a pair of opposing longitudinal knife slots 488a, 488b extending therethrough, a pair of opposing distal locking slots 481a, 481b extending therethrough, a pair of opposing proximal locking slots 471a, 471b extending therethrough, and a proximal end 491 configured to engage a suitable mechanical interface within the housing 412 to aid in proper support of the inner shaft member 480 within the housing 412 (see FIGS. 12 and 15A-15D).

The knife 402 is a generally flat, metal component defining a profile that may be constructed by a stamping process. The knife 402 supports the sharpened knife blade 456 at a distal-most end thereof. The sharp edge of the knife blade 456 may be applied to the distal end of the knife 402 subsequent to the stamping process that forms the profile. For example, various manufacturing techniques may be employed such as grinding, coining, electrochemical etching, electropolishing, or other suitable manufacturing processes, for forming sharpened edges. A longitudinal slot 406 is defined within the knife 402 to provide clearance for the pivot pin 444, the cam pin 492, and the key member 494. A proximal through bore 408a extends through a proximal portion 408 of the knife 402 and provides a mechanism for operatively coupling the knife 402 to the trigger 426 via the dowel pin 493. The connection between the knife 402 and the trigger 426 is described in detail below with reference to FIGS. 12, 13, 14A, and 14B.

Figure 4:
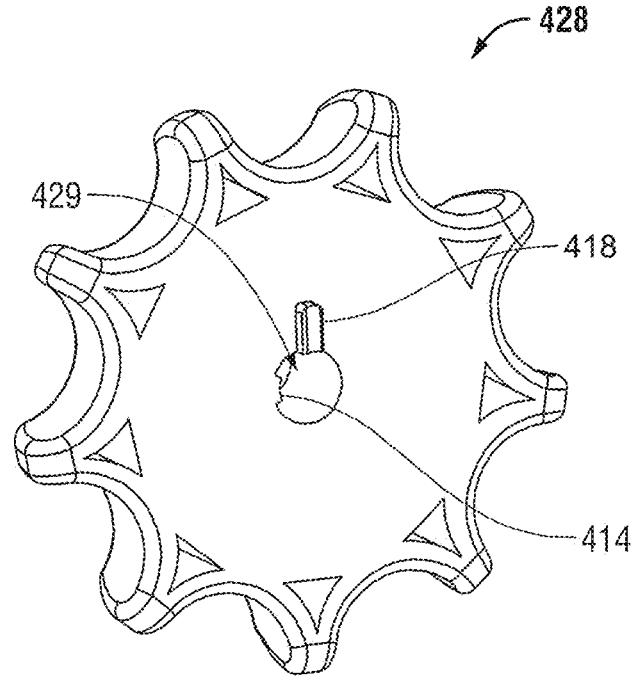
FIG. 4 is a proximally-facing perspective view of a rotation knob depicting a cavity for receiving the elongated shaft of FIG. 1.

Referring now to FIG. 4, the rotation knob 428 includes a passageway 429 defined therethrough for receiving the outer shaft member 460. The passageway 429 has a generally circular profile corresponding to the circular profile of the outer shaft member 460. The passageway 429 includes a longitudinal keying member 414 that is configured to align with and be seated within longitudinal slot 469 (FIG. 3A) of the outer shaft member 460. The keying member 414 projects laterally inward along the length of passageway 429 such that the insertion of the proximal end of the outer shaft member 460 into the passageway 429 of the rotation knob 428 operatively couples the outer shaft member 460 to the rotation knob 428 and, thus, permits longitudinal motion of the inner shaft member 480 therethrough.

In one embodiment, a cable clearance passageway (not shown) is defined through rotation knob 428 to permit passage of electrical cables or wires that electrically couple the scaling plates 448, 450 to the electrosurgical generator 443 (FIG. 1). Rotational motion imparted to the rotation knob 428 may thus impart rotational motion to each of the components of the elongated shaft 416, and to the end effector 414, which is coupled thereto.

Figure 13:
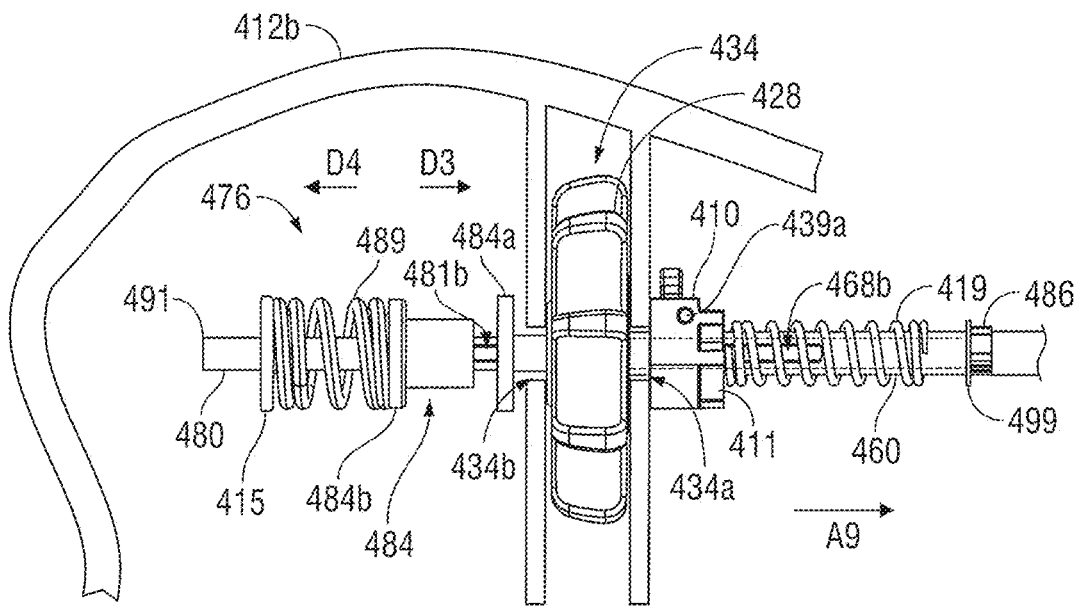
FIG. 13 is a partial, side view of a proximal portion of the jaw actuation mechanism of FIG. 6 depicting a connection between the jaw actuation mechanism and the jaw drive rod mechanism for imparting longitudinal movement to the jaw drive rod.

As shown in FIG. 13, the rotation knob 428 is seated within an interior compartment 434 of the housing 412 and, as shown in FIG. 1, extends laterally outward from opposing sides of the housing 412 (only shown extending laterally outward from housing half 412b). The interior compartment 434 defines distal and proximal passageways 434a and 434b that permit the passage of the components of the elongated shaft 416 therethrough. The rotational motion of the rotation knob 428 may be limited by a stop boss 418 projecting distally from the rotation knob 428 (FIG. 4). The stop boss 418 is positioned to engage the distal passage 434a of the compartment 434 to restrict rotational motion of the rotation knob 428. For example, in some embodiments, the stop boss 418 may engage the distal passage 434a to restrict rotational motion of the rotation knob 428 to 180 degrees in either direction.

Figure 5:
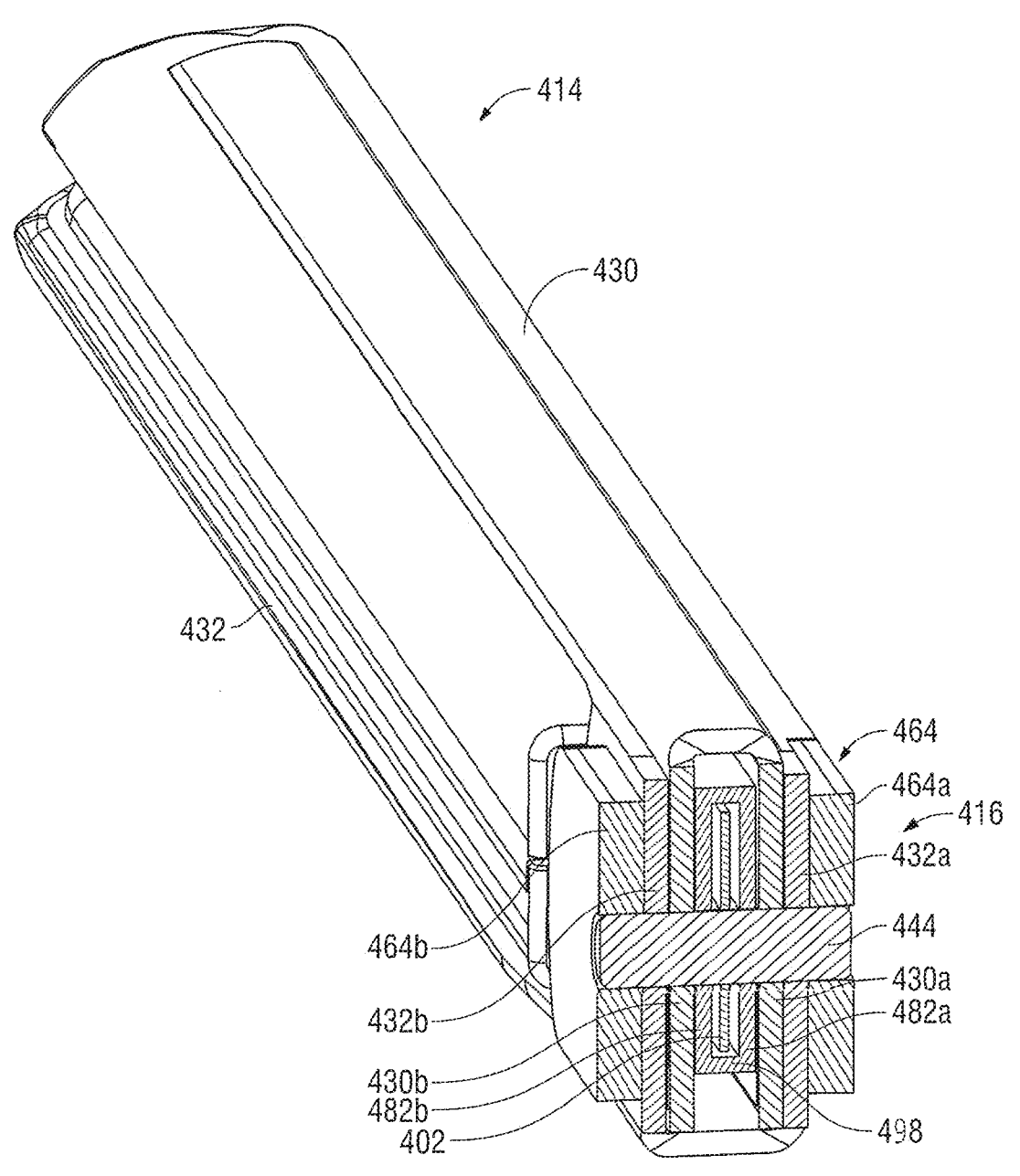
FIG. 5 is a cross-sectional, perspective view of the end effector assembled with the elongated shaft of FIG. 1.

Referring now to FIG. 5, the end effector 414 is coupled to the distal end of the elongated shaft 416 by the pivot pin 444. The pivot pin 444 is coupled to the sidewalls 464a and 464b of the clevis 464 defined at the distal end of the outer shaft member 460. Thus, the pivot pin 444 represents a longitudinally stationary reference for the longitudinal movements of inner shaft member 480 and the knife 402. Laterally inward of the sidewalls 464a, 464b, the pivot pin 444 extends through the flags 432a, 432b of the lower jaw member 432, the flags 430a and 430b of the upper jaw member 430, the sidewalls 482a, 482b of the knife guide 498, and the knife 402. The jaw members 430, 432 are free to pivot about the pivot pin 444, and the inner shaft member 480 and the knife 402 are free to translate longitudinally around the pivot pin 444.

Figure 6:
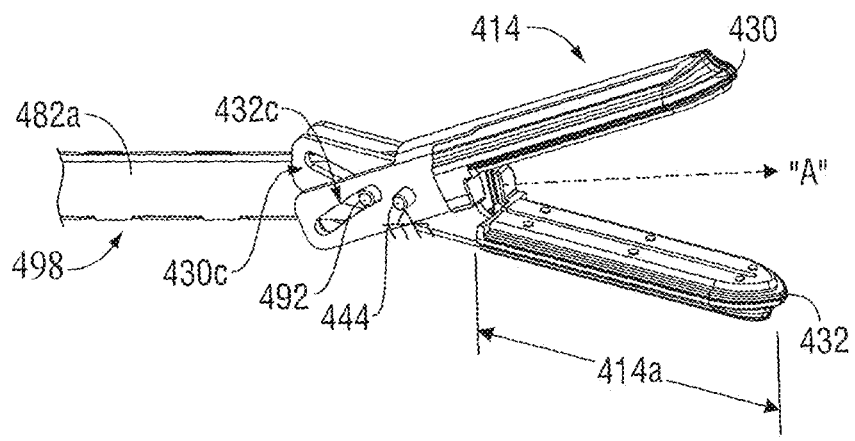
FIG. 6 is a partial, perspective view of a distal portion of a jaw actuation mechanism of the end effector of FIG. 1.

Referring now to FIG. 6, the end effector 414 is shown in the open configuration. Since the knife guide 498 is coupled to the cam pin 492, when the inner shaft member 480 is in the distal position, the cam pin 492 is located in a distal position in cam slots 430c and 432c defined through the flags 430a, 430b, 432a, 432b of the jaw members 430, 432, respectively.

The inner shaft member 480 may be drawn proximally relative to the pivot pin 444 to move the end effector 414 to the closed configuration (see FIG. 2B). Since the longitudinal position of the pivot pin 444 is fixed (by the outer shaft member 460, which is removed from view in FIG. 6 for clarity), and since the cam slots 430c, 432c are obliquely arranged with respect to the longitudinal axis A-A, proximal retraction of the cam pin 492 through the cam slots 430c, 432c induces the jaw members 430, 432 to pivot toward one another about the pivot pin 444. Conversely, when the end effector 414 is in the closed configuration, longitudinal translation of the inner shaft member 480 in a distal direction induces the jaw members 430, 432 to pivot away from one another toward the open configuration.

Figure 7:
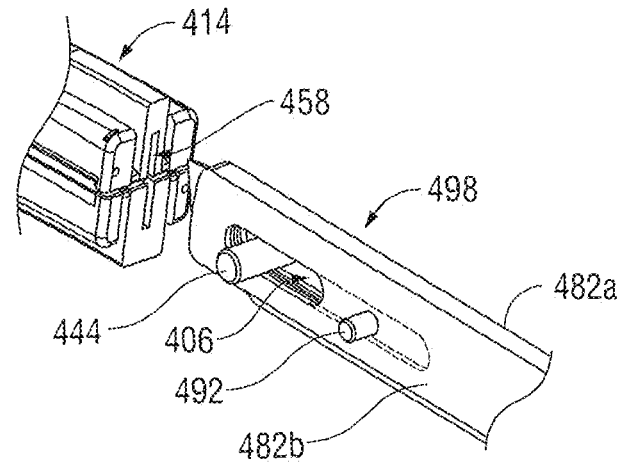
FIG. 7 is a partial, perspective view of distal portion of a knife actuation mechanism of the end effector of FIG. 1.

Referring now to FIG. 7, the longitudinal slot 406 in the knife 402 extends around both the pivot pin 444 and the cam pin 492, and thus the pins 444, 492 do not interfere with the reciprocal motion of the knife 402. The pivot pin 444 and cam pin 492 extend through the slot 406 in such a manner as to guide longitudinal motion of the knife 402 as well as constrain vertical motion of the knife 402. The blade 456 at the distal-most end of the knife 402 is centrally aligned by the knife guide 498, as discussed hereinabove. Properly aligned, the blade 456 readily enters the knife channel 458 defined in the jaw members 430, 432.

Referring now to FIGS. 8 and 9, the lower jaw member 432 is constructed of three major components. These components include a double-flag jaw insert 440, an insulator 442 and the sealing plate 448. The flags 432a, 432b of the jaw member 432 define a proximal portion of the double-flag jaw insert 440, and a generally u-shaped channel 444 extends distally to support the tissue engaging portion of the jaw member 432. The double-flag jaw insert 440 includes various planar surfaces, and may be constructed as a sheet metal component formed by a stamping process. In such a stamping process, the cam slots 432c and pivot holes 432d may be punched into a flat blank, and subsequently the blank may be bent to form the flags 432a, 432b and the u-shaped channel 444.

The insulator 442 may be constructed of an electrically insulative plastic such as a polyphthalamide (PPA) (e.g., Amodel®), polycarbonate (PC), acrylonitrile butadiene styrene (ABS), a blend of PC and ABS, nylon, ceramic, etc. The electrically insulative plastic may be overmolded onto the jaw insert 440 in a single-shot injection molding process such that sealing plate 448 is overmolded to the jaw insert 440. Additionally or alternatively, the electrically insulative plastic may be mechanically coupled to the jaw insert 440, e.g., pressed, snapped, glued, etc. Various features may be molded into the insulator 442 that facilitate the attachment of the sealing plate 448 to the insert 440. For example, tabs may be provided that permit a snap-fit attachment of the sealing plate 448, or ridges may formed that permit ultrasonic welding of the sealing plate 448 onto the insulator 442. The sealing plate 448 may be constructed of an electrically conductive metal, and may be stamped from a flat sheet stock.

Referring now to FIG. 10, the flags 430*a*, 430*b* of the upper jaw member 430 are depicted schematically in a nestled configuration with respect to the flags 432*a*, 432*b* of the lower jaw member 432. The proximal portion of the upper jaw member 430 is narrower than the proximal portion of the lower jaw member 432, and thus, a lateral spacing "S" between the flags 432*a*, 432*b* is sufficient to permit the flags 430*a* and 430*b* to be positioned therebetween. A pivot axis "P0" extends through an overlapping portion of the flags 430*a*, 432*a*, and 430*b*, 432*a* such that the upper and lower jaw members 430, 432 may pivot about the common axis "P0." In the nestled configuration, the proximal portions of the upper and lower jaw members 430, 432 also share a common centerline "CL-1" that is transverse with respect to the pivot axis "P0."

An alternative to the nestled configuration illustrated in FIG. 10 is the offset configuration illustrated schematically in FIG. 11. A proximal portion of double-flag upper jaw member 450 includes flags 450*a* and 450*b*. A proximal portion of a double-flag lower jaw member 452 includes flags 452*a* and 452*b* and exhibits a width that is identical to a width of the proximal portion of the upper jaw member 450. To provide an overlapping portion of the flags 450*a*, 452*a* and 450*b*, 452*b* such that the jaw members 450, 452 may pivot about the common axis "P0," one flag 450*a* of the upper jaw member 450 is positioned on a laterally exterior side of the corresponding flag 452*a* of the lower jaw member 452, and the other flag 450*b* of the upper jaw member 450 is positioned on a laterally interior side of the corresponding flag 452*b* of the lower jaw member 452. In the offset configuration, a centerline "CL-2" of the proximal portion of the upper jaw member 450 is laterally offset with respect to a centerline "CL-3" of the lower jaw member 452.

Figure 12:
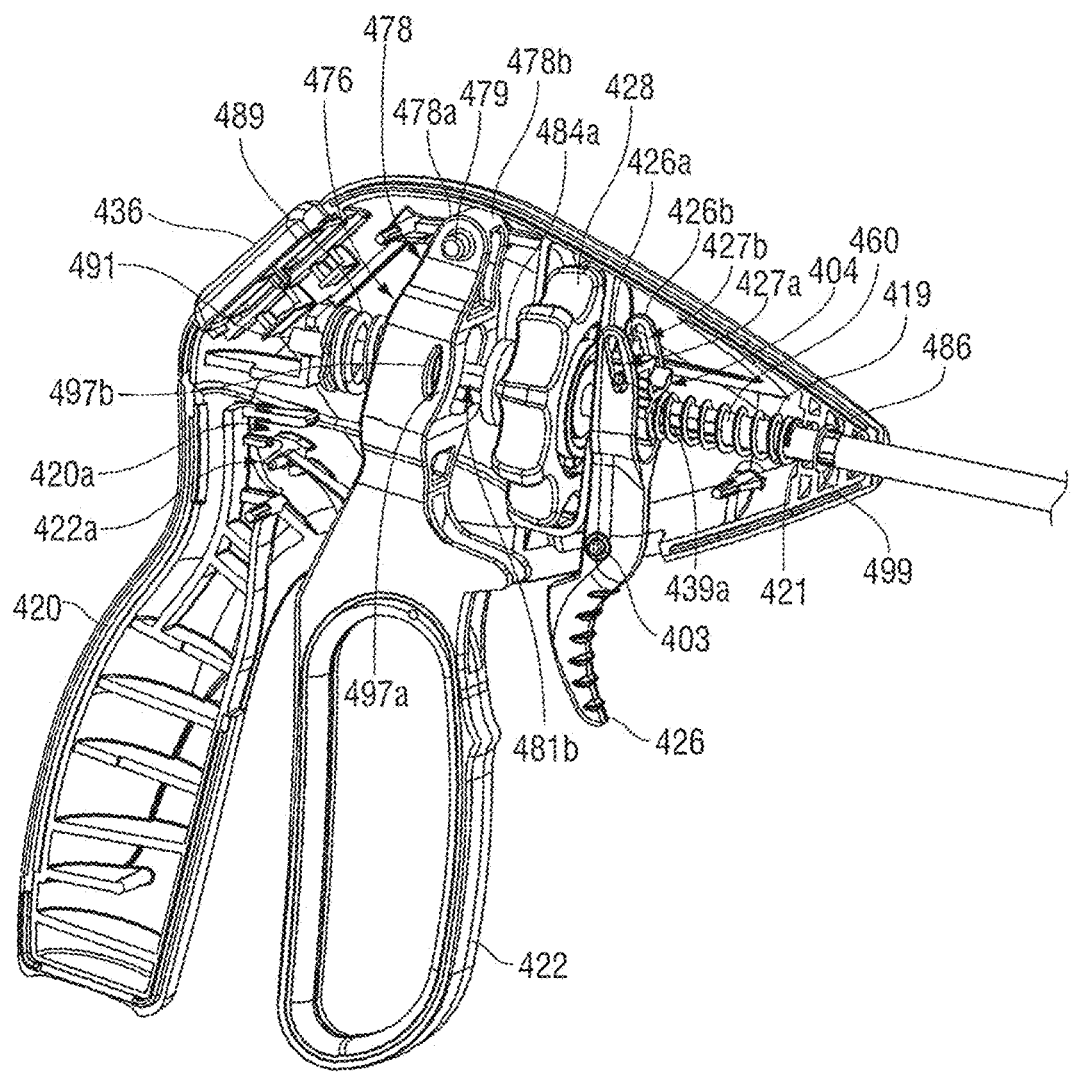
FIG. 12 is a perspective view of a proximal portion of the instrument of FIG. 1 with a portion of the housing removed revealing internal components.

Referring now to FIG. 12, the connection of the movable handle 422 and the knife trigger 426 to the longitudinally movable components of the elongated shaft 416 is described. The movable handle 422 may be manipulated to impart longitudinal motion to the inner shaft member 480, and the knife trigger 426 may be manipulated to impart longitudinal motion to the knife 402. As discussed above, longitudinal motion of the inner shaft member 480 serves to move the end effector 414 between the open configuration of FIG. 2A and the closed configuration of FIG. 2B, and longitudinal motion of the knife 402 serves to move knife blade 456 through knife channel 458 (FIG. 2A).

The movable handle 422 is operatively coupled to the inner shaft member 480 by a connection mechanism 476 (FIG. 12). The connection mechanism 476 includes a clevis 478 defined at an upper end of the movable handle 422. The clevis 478 is pivotally supported on the left housing half 412*b* by a pivot boss 479. A second complementary pivot boss (not shown) is provided on the right housing half 412*a* to support the clevis 478. Each of two upper flanges 478*a* and 478*b* of the clevis 478 extend upwardly about opposing sides of a drive collar 484 supported on the inner shaft member 480 and include rounded drive surfaces 497*a* and 497*b* thereon. Drive surface 497*a* engages a proximal-facing surface of a distal lock collar 484*a* and drive surface 497*b* engages a distal facing surface of a proximal rim 484*b* of the drive collar 484 (FIG. 13). The distal lock collar 484*a* engages the opposing distal locking slots 481*a*, 481*b* (FIG. 3A) extending through the proximal portion 488 of the inner shaft member 480 to lock-fit the distal lock collar 484*a* to the inner shaft member 480. Thus, the distal lock collar 484*a* is prevented from longitudinal motion relative to the inner shaft member 480. Drive surface 497*a* is arranged along the longitudinal axis A-A such that pivotal motions of the movable handle 422 about the pivot bosses 479 induce corresponding longitudinal motion of the drive collar 484 along the longitudinal axis A-A in the proximal direction. Drive surface 497*b* is arranged along the longitudinal axis A-A such that pivotal motions of the movable handle 422 about the pivot bosses 479 induce corresponding longitudinal motion of the distal lock collar 484*a* along the longitudinal axis A-A in the distal direction.

Referring now to FIG. 13, proximal longitudinal motion may be imparted to the inner shaft member 480 by pushing the proximal rim 484*b* of the drive collar 484 proximally with the movable handle 422 (FIG. 12) as indicated by arrow D4. The proximal rim 484*b* engages a spring 489 that is constrained between the proximal rim 484*b* and a proximal lock collar 415. The proximal lock collar 415 engages the opposing proximal locking slots 471*a*, 471*b* (FIG. 3A) extending through the proximal portion 488 of the inner shaft member 480 to lock-fit the proximal lock collar 415 to the inner shaft member 480. Thus, the proximal lock collar 415 is prevented from longitudinal motion relative to the inner shaft member 480 and serves as a proximal stop against which spring 489 compresses.

Distal longitudinal motion is imparted to the inner shaft member 480 by pushing the distal lock collar 484*a* distally with drive surface 497*a* of movable handle 422 as indicated by arrow D3 (FIG. 13). Distal longitudinal motion of the distal lock collar 484*a* induces a corresponding distal motion of the inner shaft member 480 by virtue of the lock-fit coupling of the distal lock collar 484*a* to the opposing proximal locking slots 471*a*, 471*b* extending through the proximal portion 488 of the inner shaft member 480 (FIG. 3A).

Proximal longitudinal motion of the inner shaft member 480 draws the cam pin 492 proximally to pivot the jaw members 430, 432 toward one another to move the end effector 414 to the closed configuration as described above with reference to FIG. 6. Once the jaw members 430 and 432 are closed, the inner shaft member 480 essentially bottoms out (i.e., further proximal movement of the inner shaft member 480 is prohibited since the jaw members 430, 432 contact one another). Further proximal movement of the movable handle 422 (FIG. 12), however, will continue to move the drive collar 484 proximally. This continued proximal movement of the drive collar 484 further compresses the spring 489 to impart additional force to the inner shaft member 480, which results in additional closure force applied to tissue grasped between the jaw members 430, 432 (see FIG. 2B). The spring 489 also serves to bias the movable handle 422 to an open configuration such that the movable handle 422 is separated from the stationary handle 420.

Referring again to FIG. 12, the trigger 426 is pivotally supported in the housing 412 about a pivot boss 403 protruding from the trigger 426. The trigger 426 is operatively coupled to the knife 402 by a knife connection mechanism 404 such that pivotal motion of the trigger 426 induces longitudinal motion of the knife 402. The knife connection mechanism 404 includes upper flanges 426*a*, 426*b* of the trigger 426 and a knife collar 410.

Figures 14A, 14B:
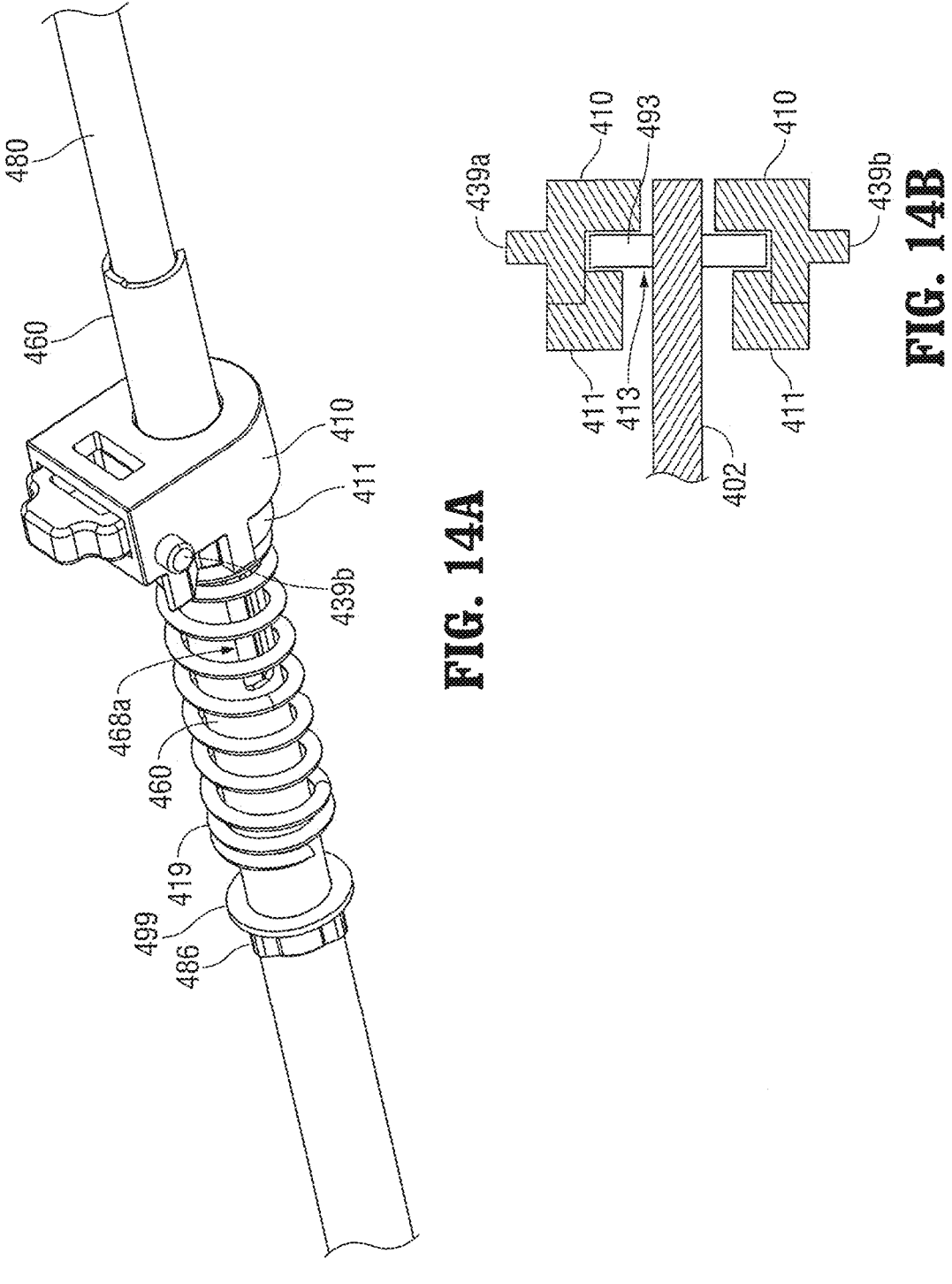
FIG. 14A is a perspective view of a proximal portion of the knife actuation mechanism of the end effector of FIG. 1.
FIG. 14B is a cross-sectional, top view of a knife collar of the knife actuation mechanism of the end effector of FIG. 1.

Referring now to FIGS. 13, 14A, and 14B, the knife collar 410 includes a cap member 411 coupled thereto and a pair of integrally formed pin bosses 439*a*, 439*b* extending from opposing sides thereof. The knife collar 410 may include indentations or catches defined therein (not shown) that receive corresponding snap-in features (e.g., arms) of the cap member 411. The cap 411 may thus be assembled to the knife collar 410 such that the cap 411 and the knife collar 410 translate together. As shown by FIG. 14B, the coupling of the knife collar 410 to the cap 411 forms an interior circular channel 413 to capture the dowel pin 493 therein such that the dowel pin 493 is supported on opposing ends between the knife collar 410 and the cap 411. The dowel pin 493 extends through the proximal through bore 408*a* extending through a proximal portion 408 of the knife 402 (FIG. 3A) to operably couple the knife 402 to the knife collar 410. Upon longitudinal motion of the inner shaft member 480, dowel pin 493 translates longitudinally within knife slots 488*a*, 488*b*, respectively, of the inner shaft member 480 such that the longitudinal motion of inner shaft member 480 is unimpeded by dowel pin 493. Upon rotation of the elongated shaft 416 and end effector 414 about the longitudinal axis A-A via the rotation knob 428 (FIG. 1), dowel pin 493 freely rotates within the interior circular channel 413 such that the outer and inner shaft members 460 and 480 (removed from view in FIG. 14B for clarity), the knife 402, and the dowel pin 493 rotate within the knife collar 410 about the longitudinal axis A-A. In this way, the knife collar 410 serves as a stationary reference for the rotational movement of the outer shaft member 460, the inner shaft member 480, the knife 402, and the dowel pin 493.

Referring again to FIG. 12, the upper flanges 426*a*, 426*b* of the trigger 426 include respective slots 427*a*, 427*b* defined therethrough that are configured to receive the pin bosses 439*a*, 439*b*, respectively, of the knife collar 410 such that pivotal motion of the trigger 426 induces longitudinal motion of the knife collar 410 and, thus, the knife 402 by virtue of the coupling of knife 402 to the knife collar 410 via the dowel pin 493 extending through the through bore 408*a*. During longitudinal motion of the knife collar 410, dowel pin 493 translates longitudinally within the opposing slots 468*a*, 468*b* of the outer shaft member 460 and the slots 488*a*, 488*b* of the inner shaft member 480.

Referring now to FIGS. 13 and 14A, when the trigger 426 is moved to induce motion of the knife collar 410 in order to translate the blade 456 through the knife channel 458, the knife collar 410 translates along the outer shaft member 460 in the direction of arrow A9 to abut a spring 419 such that spring 419 compresses against a distal portion 421 of the interior of the housing 412 (FIG. 12). The spring 419 biases the knife collar 410 in a proximal direction to a proximal position along the outer shaft member 460.

Figure 15A:
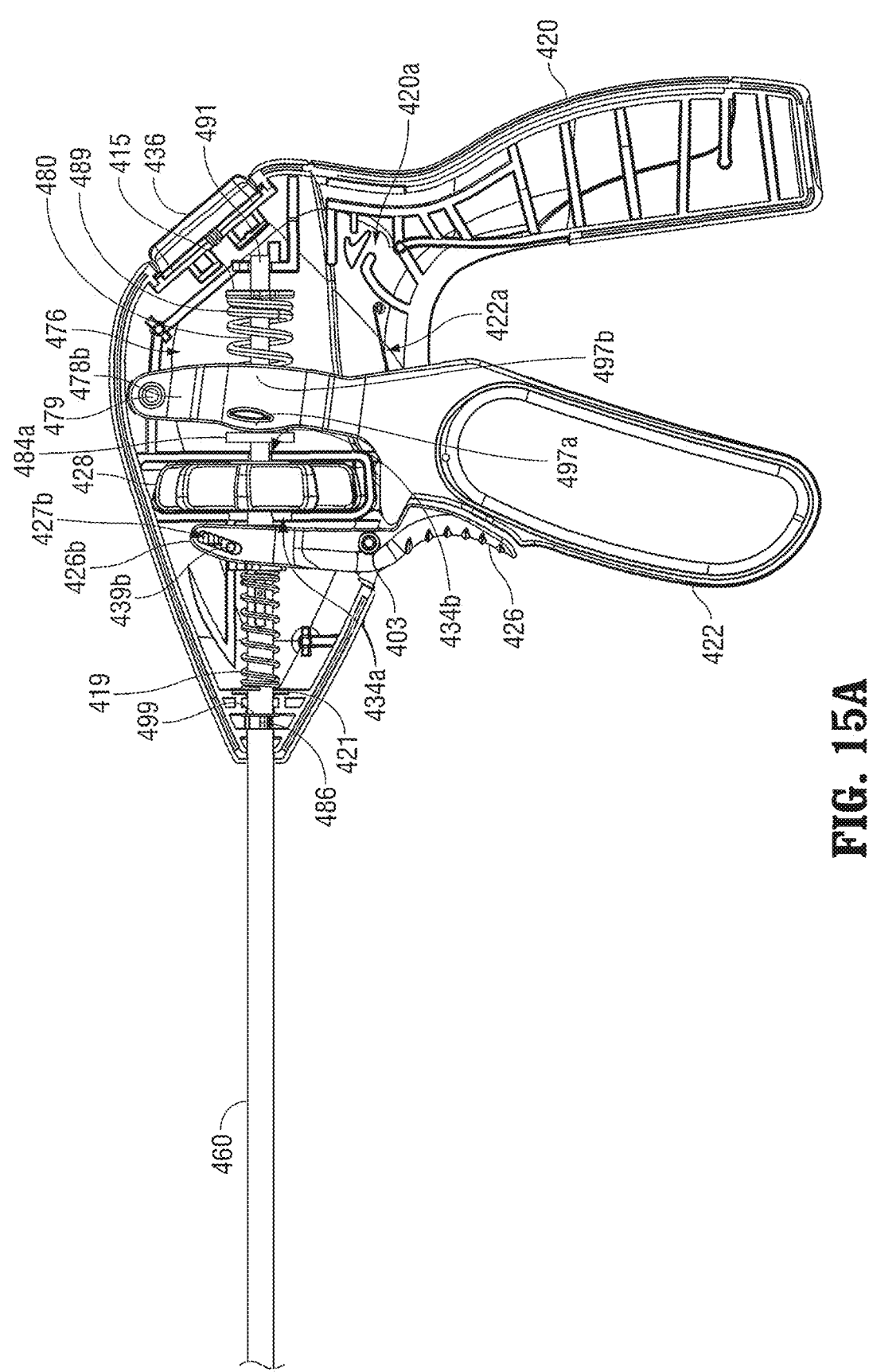
FIG. 15A is a side view of the proximal portion of the instrument of FIG. 12 depicting a movable handle in a separated position with respect to a stationary handle, which corresponds to the open configuration of the end effector depicted in FIG. 2A, and a knife trigger in a separated configuration with respect to the stationary handle, which corresponds to an un-actuated or proximal configuration of a knife with respect to the jaw members.

Referring now to FIGS. 15A, 15B, 15C and 15D, a sequence of motions may be initiated by moving the movable handle 422 to induce motion of the jaw drive mechanism in order to close the jaws 430, 432, and by moving the trigger 426 to induce motion of the knife collar 410 in order to translate the blade 456 through the knife channel 458. Initially, both the moveable handle 422 and the knife trigger 426 are in a distal or un-actuated position as depicted in FIG. 15A. This arrangement of the moveable handle 422 and trigger 426 sustains the end effector 414 in the open configuration (FIG. 2A) wherein the jaw members 430, 432 are substantially spaced from one another, and the knife blade 456 is in a retracted or proximal position with respect to the jaw members 430, 432. The initial distal position of the trigger 422 is actively maintained by the influence of the spring 419 on the knife collar 410. The distal position of the moveable handle 422, however, is only passively maintained, e.g., by internal friction within the jaw actuation mechanism. When both the moveable handle 422 and the knife trigger 426 are in the distal, un-actuated position, pivotal motion of the knife trigger 426 in a proximal direction, i.e., toward the stationary handle 420, is prohibited by interference between the trigger 426 and moveable handle 422. This interference prohibits advancement of the knife blade through the knife channel 458 when the end effector 414 is in the open configuration.

Figure 15B:
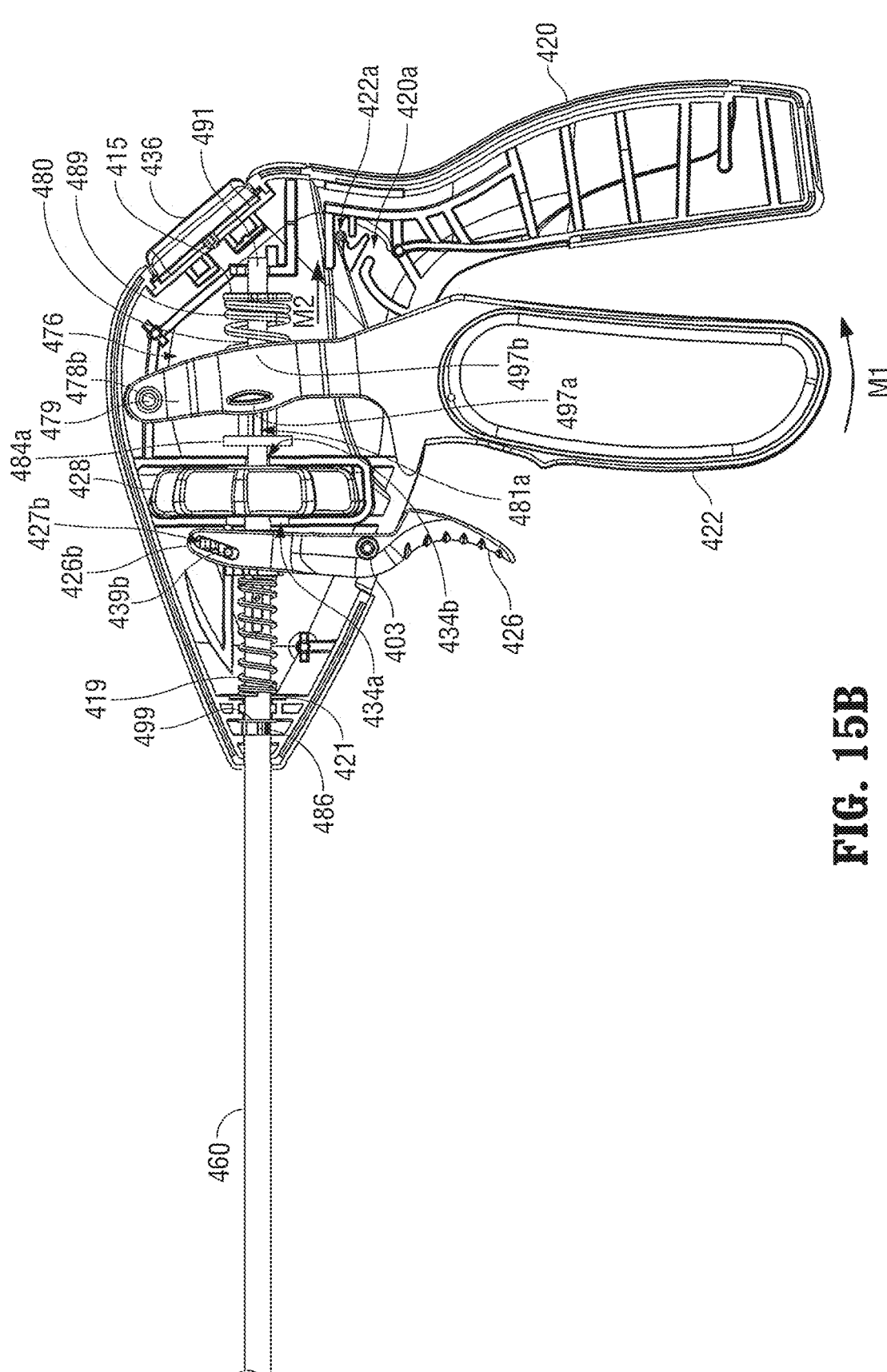
FIG. 15B is a side view of the proximal portion of the instrument of FIG. 12 depicting the movable handle in an intermediate position with respect to the stationary handle, which corresponds to a first closed configuration of the end effector wherein the jaw members encounter one another.

The movable handle 422 may be moved from the distal position of FIG. 15A to the intermediate position depicted in FIG. 15B to move the jaw members 430, 432 to the closed configuration (FIG. 2B). As the movable handle 422 pivots about the pivot boss 479 in the direction of arrow M1 (FIG. 15B), the drive surface 497*b* of the movable handle 422 engages the proximal rim 484*b* of the drive collar 484. The drive collar 484 and the spring 489 are both driven proximally against the proximal lock collar 415 and, thus, the inner shaft member 480 is driven proximally in the direction of arrow M2 (FIG. 15B). As discussed above with reference to FIG. 6, proximal movement of the inner shaft member 480 serves to draw the cam pin 492 proximally though the cam slots 430*c*, 432*c* of the jaw members 430, 432, respectively, and thus pivot the jaw members 430, 432 toward one another. As the jaw members 430, 432 engage one another and no further pivotal movement of the jaw members 430, 432 may be achieved, the jaw actuation mechanism "bottoms out" and further proximal movement of the cam pin 492 and the inner shaft member 480 is prevented.

Figure 15C:
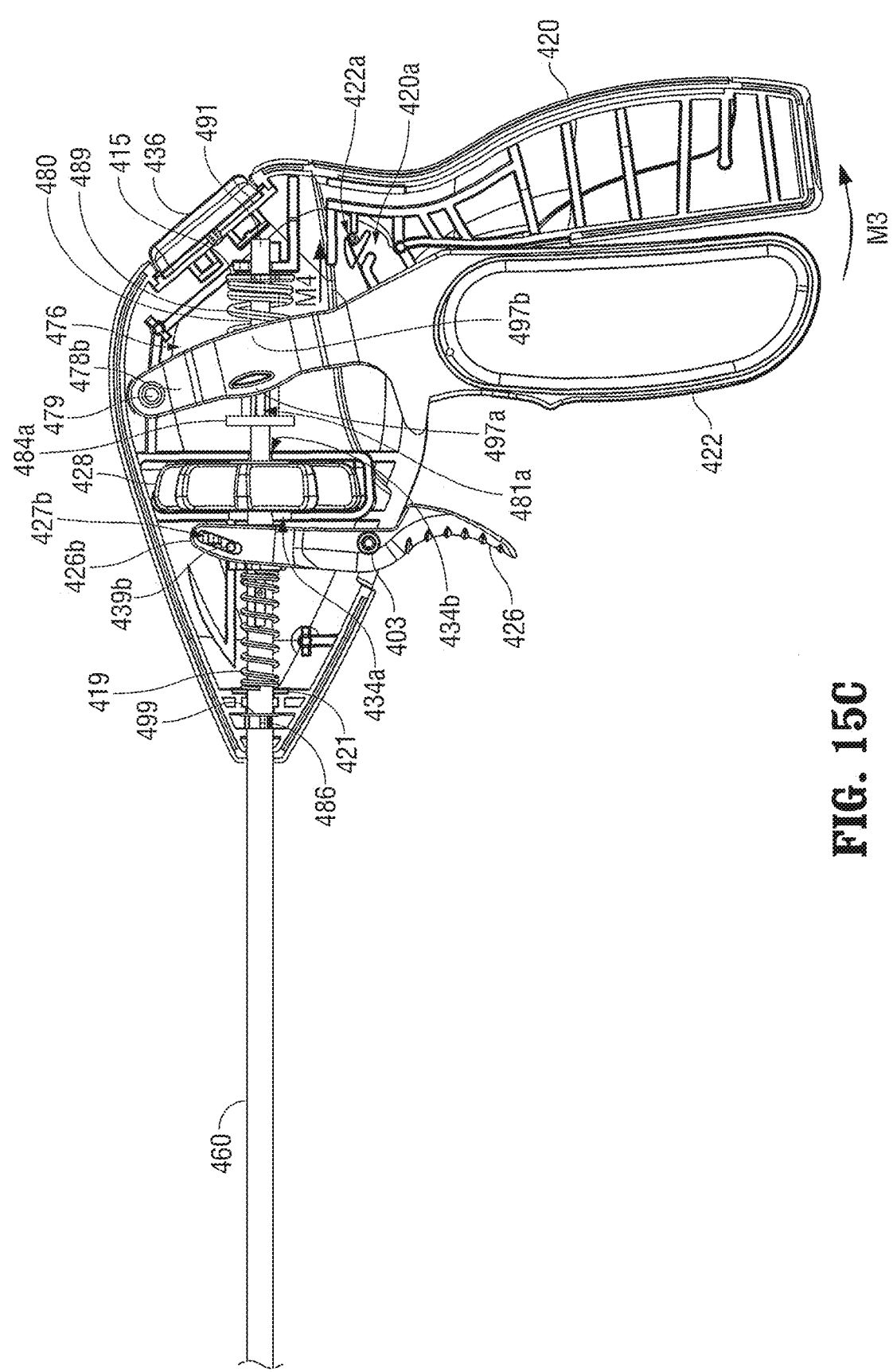
FIG. 15C is a side view of the proximal portion of the instrument of FIG. 12 depicting the movable handle in an approximated configuration with respect to the stationary handle, which corresponds to a second closed configuration of the end effector wherein the jaw members apply an appropriate pressure to generate a tissue seal.

The movable handle 422 may be moved from the intermediate position of FIG. 15B to the actuated or proximal position of FIG. 15C to increase the pressure applied by the jaw members 430, 432. As the movable handle 422 pivots further about the pivot boss 479 in the direction of arrow M3 (FIG. 15C), the drive surface 497*b* presses the proximal rim 484*b* of the drive collar 484 further distally against the spring 489 in the direction of arrow M4 (FIG. 15C). The spring 489 is compressed against the proximal lock collar 415, and a tensile force is transmitted through the inner shaft member 480 to the jaw members 430, 432. The tensile force supplied by the spring 489 ensures that the jaw members 430, 432 apply an appropriate pressure to effect a tissue seal. When the movable handle 422 is in the actuated or proximal position, electrosurgical energy may be selectively supplied to the end effector 414 to generate a tissue seal.

When the movable handle 422 is in the actuated or proximal position, a t-shaped latch 422*a* extending proximally from an upper portion of the moveable handle 422 is received in a railway 420*a* supported within the stationary handle 420. The railway 420*a* serves to temporarily lock the movable handle 422 in the proximal position against the bias of the spring 489. Thus, the railway 420*a* permits the maintenance of pressure at the end effector 414 without actively maintaining pressure on the movable handle 422. The flange 422*a* may be released from the railway 420*a* by pivoting the movable handle 422 proximally and releasing the movable handle 422 to move under the influence of the spring 489. Operation of the railway 420*a* is described in greater detail in U.S. patent application Ser. No. 11/595,194 to Hixson et al., now U.S. Pat. No. 7,766,910. In some embodiments (not shown), the latch 422*a* and the railway 420*a* may be eliminated to provide an instrument without the temporary locking capability provided by these features.

Figure 15D:
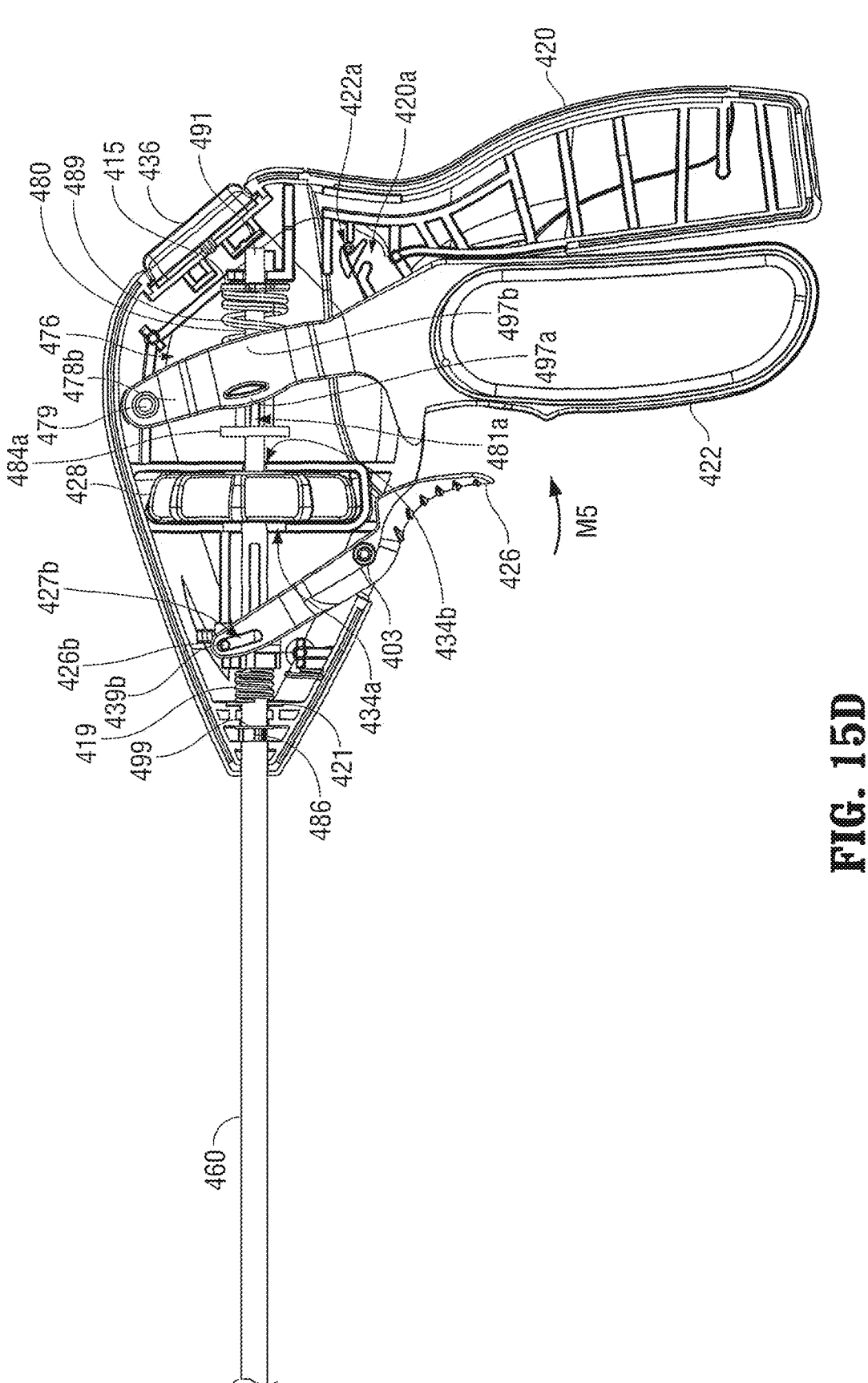
FIG. 15D is a side view of the proximal portion of the instrument of FIG. 12 depicting the knife trigger in an actuated configuration, which corresponds to an actuated or distal position of the knife with respect to the jaw members.

When the movable handle 422 is in the actuated or proximal position, the knife trigger 426 may be selectively moved from the distal position of FIG. 15C to the proximal position of FIG. 15D to advance the knife blade 456 distally through knife channel 458. The knife trigger 426 may be pivoted in the direction of arrow M5 (FIG. 15D), about pivot boss 403 to advance the flange 426*b* of the knife trigger 426 distally in the direction of arrow M6 such that the pin boss 439*b* translates within slot 427*b* from the position shown in FIGS. 15A-15C to the position shown in FIG. 15D. Although not explicitly shown in FIGS. 15A-15D, pin boss 439*a* translates within slot 427*a* in the same manner as described above with respect to pin boss 439*b* and slot 427*b*. Movement of flanges 426*a*, 426*b* draws the knife collar 410 distally, which induces distal longitudinal motion of the knife 402 by virtue of the coupling of knife 402 to the knife collar 410 via the dowel pin 493 extending through the through bore 408*a*, as described above with reference to FIGS. 3A and 14B.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. An electrosurgical instrument, comprising:
a housing;
an elongated shaft extending from the housing and defining a longitudinal axis;
a pair of jaw members disposed at a distal portion of the elongated shaft, wherein at least one of the jaw members of the pair of jaw members is movable relative to the other jaw member of the pair of jaw members;
a knife collar disposed within the housing and configured to move longitudinally along the elongated shaft, the knife collar including an interior channel; and
a knife having a proximal portion disposed within the interior channel of the knife collar such that the proximal portion of the knife is rotatable within the interior channel of the knife collar about the longitudinal axis and longitudinal movement of the knife collar along the longitudinal axis induces corresponding longitudinal movement of the knife.

2. The electrosurgical instrument according to claim 1, wherein the knife collar remains rotationally stationary during rotation of the proximal portion of the knife within the interior channel of the knife collar.

3. The electrosurgical instrument according to claim 1, wherein the knife collar remains rotationally stationary during rotation of the elongated shaft about the longitudinal axis.

4. The electrosurgical instrument according to claim 1, further comprising a cap attached to the knife collar, wherein the proximal portion of the knife is captured between the knife collar and the cap.

5. The electrosurgical instrument according to claim 1, further comprising a pin extending through a through bore defined by the proximal portion of the knife, wherein the pin is configured to rotate within the interior channel of the knife collar during rotation of the knife about the longitudinal axis.

6. The electrosurgical instrument according to claim 5, wherein the pin translates longitudinally through at least one slot defined through the elongated shaft during longitudinal movement of the knife collar along the longitudinal axis.

7. The electrosurgical instrument according to claim 1, further comprising a trigger coupled to the housing, wherein the knife collar defines at least one boss that couples to the trigger such that actuation of the trigger causes longitudinal movement of the knife collar and the knife along the longitudinal axis.

8. An electrosurgical instrument, comprising:
a housing;
an elongated shaft extending from the housing and defining a longitudinal axis;
a pair of jaw members disposed at a distal portion of the elongated shaft, wherein at least one of the jaw members of the pair of jaw members is movable relative to the other jaw member of the pair of jaw members;
a knife configured to cut tissue disposed between the pair of jaw members; and
a knife collar housing a proximal portion of the knife and configured to move along the longitudinal axis relative to the elongated shaft, wherein the proximal portion of the knife is rotatable relative to the knife collar and longitudinal movement of the knife collar along the longitudinal axis induces corresponding longitudinal movement of the knife.

9. The electrosurgical instrument according to claim 8, wherein the knife collar includes an interior channel in which the proximal portion of the knife is disposed, the proximal portion of the knife being rotatable within the interior channel of the knife collar about the longitudinal axis such that the knife rotates relative to the knife collar.

10. The electrosurgical instrument according to claim 9, further comprising a pin extending through a through bore defined by the proximal portion of the knife, wherein the pin is configured to rotate within the interior channel of the knife collar during rotation of the knife about the longitudinal axis.

11. The electrosurgical instrument according to claim 10, wherein the pin translates longitudinally through at least one slot defined through the elongated shaft during longitudinal movement of the knife collar along the longitudinal axis.

12. The electrosurgical instrument according to claim 8, wherein the knife collar remains rotationally stationary during rotation of the elongated shaft about the longitudinal axis.

13. The electrosurgical instrument according to claim 8, further comprising a cap attached to the knife collar, wherein the proximal portion of the knife is captured between the knife collar and the cap.

14. The electrosurgical instrument according to claim 8, further comprising a trigger coupled to the housing, wherein the knife collar defines at least one boss that couples to the trigger such that actuation of the trigger causes longitudinal movement of the knife collar and the knife along the longitudinal axis.

15. An electrosurgical instrument, comprising:
a housing;
an elongated shaft extending from the housing and defining a longitudinal axis;
a pair of jaw members disposed at a distal portion of the elongated shaft, wherein at least one of the jaw members of the pair of jaw members is movable relative to the other jaw member of the pair of jaw members;

a knife configured to cut tissue disposed between the pair of jaw members;

a pin extending through the knife; and a knife collar configured to move the knife along the longitudinal axis relative to the elongated shaft, the knife collar defining an interior channel for receiving the pin, wherein the pin is rotatable within the interior channel during rotation of the knife about the longitudinal axis and relative to the knife collar.

16. The electrosurgical instrument according to claim 15, wherein the pin extends through a through bore defined by a proximal portion of the knife.

17. The electrosurgical instrument according to claim 15, wherein the pin translates longitudinally through at least one slot defined through the elongated shaft during longitudinal movement of the knife collar along the longitudinal axis.

18. The electrosurgical instrument according to claim 15, wherein the knife collar remains rotationally stationary during rotation of the elongated shaft about the longitudinal axis.

19. The electrosurgical instrument according to claim 15, further comprising a cap attached to the knife collar, wherein a proximal portion of the knife is captured between the knife collar and the cap.

20. The electrosurgical instrument according to claim 15, further comprising a trigger coupled to the housing, wherein the knife collar defines at least one boss that couples to the trigger such that actuation of the trigger causes longitudinal movement of the knife collar and the knife along the longitudinal axis.

* * * * *